(12) United States Patent
Berg et al.

(10) Patent No.: US 6,387,899 B1
(45) Date of Patent: May 14, 2002

(54) SUBSTITUTED CHROMAN DERIVATIVES

(75) Inventors: Stefan Berg, Ekerö; Mats Linderberg; Svante Ross, both of Södertälje; Seth-Olov Thorberg, Strängnäs; Bengt Ulff, Södertälje, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/171,572

(22) PCT Filed: Sep. 9, 1998

(86) PCT No.: PCT/SE98/01604

§ 371 Date: Oct. 21, 1998

§ 102(e) Date: Oct. 21, 1998

(87) PCT Pub. No.: WO99/14213

PCT Pub. Date: Mar. 25, 1999

(30) Foreign Application Priority Data

Sep. 18, 1997 (SE) ................................................. 9703378

(51) Int. Cl.$^7$ ..................... A61K 31/5377; A61P 25/00; C07D 413/12
(52) U.S. Cl. ..................... 514/235.8; 544/121; 544/129; 544/130; 544/360; 546/187; 546/196
(58) Field of Search ................................ 544/121, 129, 544/130; 514/235.8

(56) References Cited

U.S. PATENT DOCUMENTS 5,420,151 A    5/1995    Hammarberg et al.

FOREIGN PATENT DOCUMENTS

| WO | 9012795 | 11/1990 |
| WO | 9109853 | 7/1991 |
| WO | 9707120 | 2/1997 |

Primary Examiner—Robert W. Ramsuer
(74) Attorney, Agent, or Firm—White & Case LLP

(57) ABSTRACT

The present invention relates to new piperidinyl- or piperazinyl-substituted-3,4-dihydro-2H-1-benzopyran derivatives having formula (I) wherein X is N or CH; Y is $NR_2CH_2$, $CH_2NR_2$, $NR_2CO$, $CONR_2$ or $NR_2SO_2$ wherein $R_2$ is H or $C_1$–$C_6$ alkyl; $R_1$ is H, $C_1$–$C_6$ alkyl or $C_3$–$C_6$ cycloalkyl; $R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted; n is 0–4; $R_9$ is $C_1$–$C_6$ alkyl, $C_3$–$C_6$ cycloalkyl, $OCF_3$, $OCHF_2$, $OCH_2F$, halogen, $CONR_6R_7$, CN, $CF_3$, OH, $C_1$–$C_6$ alkoxy, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl; or $COR_8$; wherein $R_6$, $R_7$ and $R_8$ are as defined above, as (R)-enantiomers, (S)-enantiomers or racemates in the form of a free base or pharmaceutically acceptable salts or solvates thereof, a process for their preparation, pharmaceutical compositions containing said therapeutically active compounds and to the use of said active compounds in therapy.

(I)

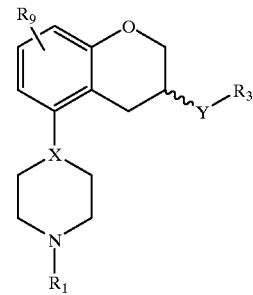

27 Claims, 1 Drawing Sheet

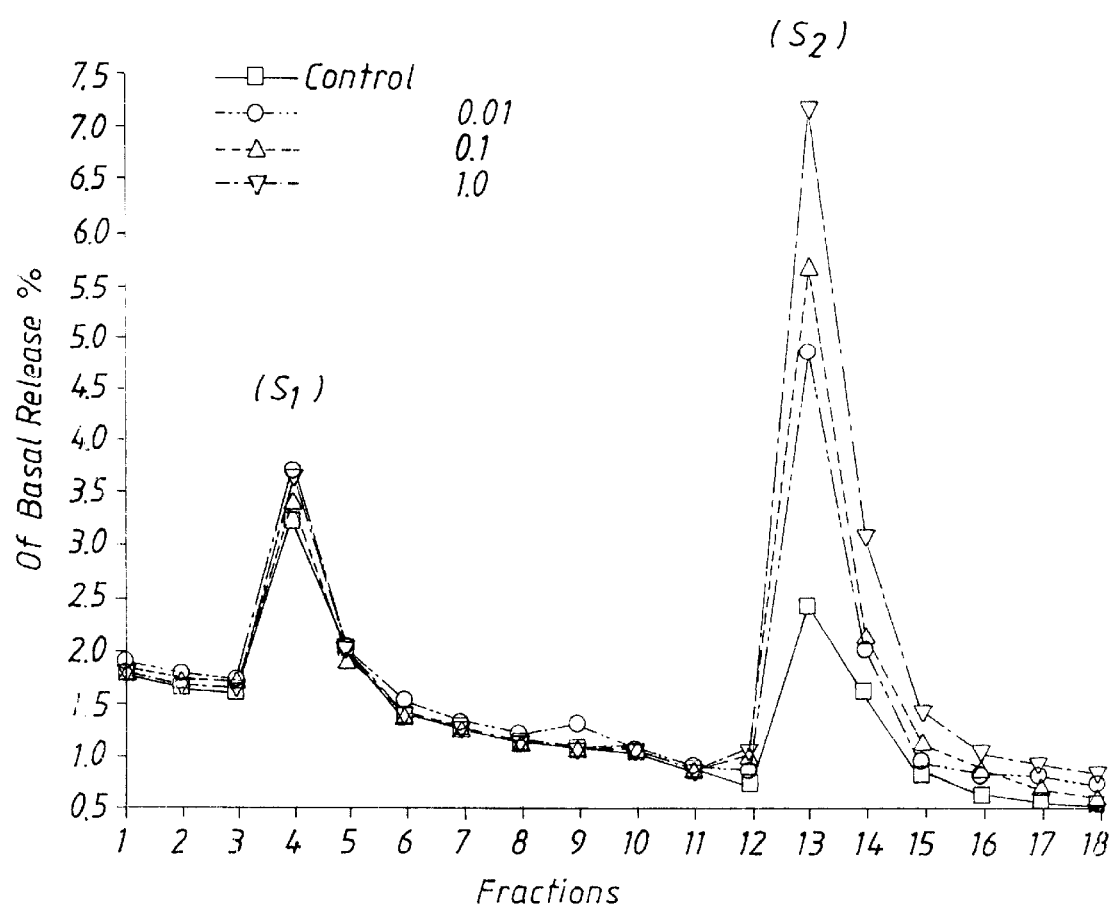

SUBSTITUTED CHROMAN DERIVATIVES

This application is the National Stage of International Application No. PCT/SE98/01604, filed Sep. 9, 1998.

FIELD OF THE INVENTION

The present invention relates to new piperidinyl- or piperazinyl-substituted 3,4-dihydro-2H-1-benzopyran derivatives as (R)-enantiomers, (S)-enantiomers or racemates in the form of free base or pharmaceutically acceptable salts or solvates thereof, a process for their preparation, pharmaceutical compositions containing said therapeutically active compounds and to the use of said active compounds in therapy.

An object of the invention is to provide compounds for therapeutic use, especially compounds having a selective effect at a subgroup of 5-hydroxytryptamine receptors, designated h5-$HT_{1B}$-receptor (previously called the 5-$HT_{1D\beta}$-receptor) in mammals including man.

It is also an object of the invention to provide compounds with a therapeutic effect after oral administration.

BACKGROUND OF THE INVENTION

Various central nervous system disorders such as depression, anxiety, etc. appear to involve the disturbance of the neurotransmitters noradrenaline (NA) and 5-hydroxytryptamine (5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients. The invention concerns compounds which have an effect on 5-HT neurotransmission.

Serotonin, or 5-HT, activity is believed to be involved in many different types of psychiatric disorders. For instance it is believed that an increase in 5-HT activity is associated with anxiety, while a decrease in 5-HT release has been associated with depression. Serotonin has in addition been implicated in such diverse conditions as eating disorders, gastrointestinal disorders, cardiovascular regulation disorders and sexual disturbances.

The 5-HT Receptors

The various effects of 5-HT may be related to the fact that serotonergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as 5-$HT_1$, 5-$HT_2$, 5-$HT_3$, 5-$HT_4$, 5-$HT_5$, 5-$HT_6$ and 5-$HT_7$ with the 5-$HT_1$ receptor further divided into the 5-$HT_{1A}$, 5-$HT_{1B}$, 5-$HT_{1D}$, 5-$HT_{1E}$ and 5-$HT_{1F}$ subtypes. Each receptor subtype is involved in a different serotonin function and has different properties.

Regulation of the 5-HT Transmission

The release of 5-HT is feedback-regulated by two different subtypes of 5-HT receptors. Inhibitory 5-$HT_{1A}$ autoreceptors are located on the cell bodies in the raphé nuclei which upon stimulation by 5-HT decrease the impulse propagation in the 5-HT neurons and thereby reducing the 5-HT released at the nerve terminals. Another subtype of inhibitory 5-HT receptors is located on the 5-HT nerve terminals, the h5-$HT_{1B}$ receptors (in rodents the r5-$HT_{1B}$ receptors) which regulate the synaptic concentration of 5-HT by controlling the amount of 5-HT that is released. An antagonist of these terminal autoreceptors thus increases the amount of 5-HT released by nerve impulses which has been shown in both in vitro and in vivo experiments.

The use of an antagonist of the terminal h5-$HT_{1B}$ autoreceptor will accordingly increase the synaptic 5-HT concentration and enhance the transmission in the 5-HT system. It would thus produce an antidepressant effect making it useful as a medication for depression.

Other localizations of h5-$HT_{1B}$ receptor subtype also exist. A large part of these postsynaptic receptors appear to be located on nerve terminals of other neuronal systems (so called heteroreceptors). Since the h5-$HT_{1B}$ receptor mediates inhibitory responses an antagonist of this receptor subtype might also increase the release of other neurotransmitters than 5-HT.

Compounds having h5-$HT_{1B}$ activity may according to well known and recognised pharmacological tests be divided into full agonists, partial agonists and antagonists.

Disclosure of the Invention

The object of the present invention is to provide compounds having a selective effect at the h5-$HT_{1B}$ receptor, preferably antagonistic properties, as well as having a good bioavailability. The effect on the other receptors chosen from, for example, the 5-$HT_{1A}$, 5-$HT_{2A}$, $D_1$, $D_2A$, $D_3$, $\alpha_1$ and $\alpha_2$ receptor has been investigated.

Accordingly, the present invention provides compounds of the formula I

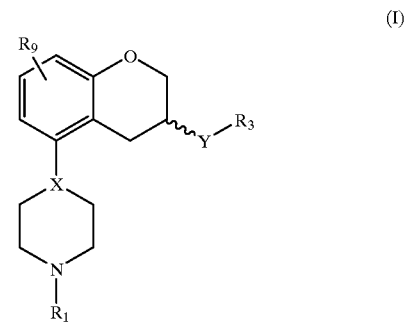

(I)

wherein
X is N or CH;
Y is $NR_2CH_2$, $CH_2NR_2$, $NR_2CO$, $CONR_2$ or $NR_2SO_2$ wherein $R_2$ is H or $C_1$–$C_6$ alkyl;
$R_1$ is H, $C_1$–$C_6$ alkyl or $C_3$–$C_6$ cycloalkyl;
$R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$;
wherein $R_4$ is H, $C_1$–$C_6$ alkyl, $C_3$–$C_6$ cycloalkyl, halogen, CN, $CF_3$, OH, $C_1$–$C_6$ alkoxy, $NR_6R_7$, $OCF_3$, $SO_3CH_3$, $SO_3CF_3$, $SO_2NR_6R_7$, phenyl, phenyl—$C_1$–$C_6$ alkyl, phenoxy, $C_1$–$C_6$ alkylphenyl, an optionally substituted heterocyclic or heteroaromatic ring containing one or two heteroatoms selected from N, O, S, SO and $SO_2$ wherein the substituent(s) is(are) selected from $C_1$–$C_6$ alkyl, $C_3$–$C_6$ cycloalkyl and phenyl—$C_1$–$C_6$ alkyl; or $COR_8$;

wherein $R_6$ is H, $C_1$–$C_6$ alkyl or $C_3$–$C_6$ cycloalkyl;
$R_7$ is H, $C_1$–$C_6$ alkyl or $C_3$–$C_6$ cycloalkyl; and
$R_8$ is $C_1$–$C_6$ alkyl, $C_3$–$C_6$ cycloalkyl, $CF_3$, $NR_6R_7$, phenyl, or a heterocyclic ring containing one or two heteroatoms selected from N, O, S, SO and $SO_2$;
wherein $R_5$ is H, OH, $CF_3$, $OCF_3$, halogen, $C_1$–$C_6$ alkyl or $C_1$–$C_6$ alkoxy;
n is 0–4;
$R_9$ is $C_1$–$C_6$ alkyl, $C_3$–$C_6$ cycloalkyl $OCF_3$, $OCHF_2$, $OCH_2F$, halogen, $CONR_6R_7$, CN, $CF_3$, OH, $C_1$–$C_6$ alkoxy, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl; or $COR_8$;
wherein $R_6$, $R_7$ and $R_8$ are as defined above,
as (R)-enantiomers, (S)-enantiomers or a racemate in the form of a free base or a pharmaceutically acceptable salt or solvate thereof which possess a high selective effect at the h5-$HT_{1B}$ receptor and also show sufficient bioavailability after oral administration.

In the present context $C_1$–$C_6$ alkyl may be straight or branched. $C_1$–$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In the present context $C_1$–$C_6$ alkoxy may be straight or branched. $C_1$–$C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

In the present context $C_3$–$C_6$ cycloalkyl may be cyclopropyl, cyclobutyl, cyclopentyl or cyclohexyl, preferably cyclohexyl.

In the present context halogen may be fluoro, chloro, bromo or iodo.

In the present context the heteroaromatic ring containing one or two heteroatoms selected from N, O or S preferably is a 5- or 6-membered heteroaromatic ring and may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl. The heteroaromatic ring can be either substituted or unsubstituted.

In the present context the heterocyclic ring containing one or two heteroatoms selected from N, O, S, SO or $SO_2$ may optionally contain a carbonyl function and is preferably a 5-, 6- or 7-membered heterocyclic ring and may be imidazolidinyl, imidazolinyl, morpholinyl, piperazinyl, piperidinyl, piperidonyl, pyrazolidinyl, pyrazolinyl, pyrrolidinyl, pyrrolinyl, tetrahydropyranyl, thiomorpholinyl, preferably piperidino, 1-piperazinyl, morpholino, thiomorpholino and 4-piperidon-1-yl.

A preferred embodiment of the invention relates to compounds of formula I wherein Y is NHCO or CONH i.e. amides. Of these compounds, the compounds wherein $R_9$ is $C_1$–$C_6$ alkyl, $C_1$–$C_6$ alkoxy, $OCHF_2$ or $OCH_2F$ and $R_3$ is unsubstituted phenyl, or mono- or di-substituted phenyl, and especially ortho-, meta- or para-substituted phenyl, and particularly these wherein the substituent $R_4$ is phenyl, phenyl—$C_1$–$C_6$ alkyl, cyclohexyl, piperidino, 1-piperazinyl, morpholino, $CF_3$, 4-piperidon-1-yl, n-butoxy or $COR_8$ wherein $R_8$ is phenyl, cyclohexyl, 4-piperidon-1-yl, 1-piperazinyl, morpholino, $CF_3$, piperidino or $NR_6R_7$, are preferred.

Examples of Combinations of Substituents are

X is N, Y is $CONR_2$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is $CH_2$-phenyl, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is phenyl, $R_4$ is piperidino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is cyclohexyl, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$.

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is piperidino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $(CH_2)_2$-phenyl, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is phenyl, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_4$ is piperidino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is $CH_2$-phenyl, $R_9$ is $OCH_3$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is morpholino, $R_9$ is $OCH_3$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $(CH_2)_2$-phenyl, $R_4$ is morpholino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_4$ is $COR_8$, $R_8$ is morpholino, $R_9$ is $OCH_3$;

X is CH, Y is $NR_2CO$, $R_1$ is H, $CH_3$, $C_2H_5$ or $C_3H_7$, $R_2$ is H, $R_3$ is phenyl, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_9$ is $R_9$ is $OCH_3$;

X is CH, Y is $CONR_2$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $OCH_3$;

X is N, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is phenyl, $R_4$ is piperidino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $(CH_2)_2$-phenyl, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_4$ is $COR_8$, $R_8$ is cyclohexyl, $R_9$ is $OCH_3$;

X is N, Y is $CONR_2$, $R_1$ is H, $CH_3$, $C_2H_5$ or $C_3H_7$, $R_2$ is H, $R_3$ is phenyl, $R_9$ is $OCH_3$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is $COR_8$, $R_8$ is $NR_6R_7$, $R_6R_7CH_3$, $C_2H_5$ or $C_3H_7$, $R_9$ is $OCH_3$;

X is N, Y is $NR_2CO$, $R_1$ is H, $CH_3$, $C_2H_5$ or $C_3H_7$, $R_2$ is H, $R_3$ is $CH_2$-phenyl, $R_9$ is $OCH_3$.

X is CH, Y is $NR_2CO$, $R_1$ is H, $CH_3$, $C_2H_5$ or $C_3H_7$, $R_2$ is H, $R_3$ is $(CH_2)_2$-phenyl, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $OCH_3$;

X is CH, Y is $NR_2CO$, $R_1$ is H, $CH_3$, $C_2H_5$ or $C_3H_7$, $R_2$ is H, $R_3$ is $(CH_2)_2$-phenyl, $R_9$ is $OCH_3$;

X is N, Y is $NR_2CO$, $R_1$ is H, $CH_3$, $C_2H_5$ or $C_3H_7$, $R_2$ is H, $R_3$ is phenyl, $R_4$ is piperidino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is phenyl, $R_4$ is piperidino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $(CH_2)_2$-phenyl, $R_9$ is $OCH_3$;

X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is $COR_8$, $R_8$ is $NR_6R_7$, $R_6R_7CH_3$, $C_2H_5$ or $C_3H_7$, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $CH_2$-phenyl, $R_4$ is phenyl, phenylmethyl or phenylethyl, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $CH_2$-phenyl, $R_4$ is morpholino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $CH_3$, $C_2H_5$ or $C_3H_7$;

X is N, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is phenyl, $R_4$ is morpholino, $R_5$ is H, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;

X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is phenyl, phenylmethyl or phenylethyl, $R_5$ is H, $R_9$ is $OCH_3$;

X is CH, Y is $CONR_2$, $R_1$ is H, $CH_3$, $C_2H_5$ or $C_3H_7$, $R_2$ is H, $R_3$ is $CH_2$-phenyl, $R_9$ is $OCH_3$;

X is N, Y is $NR_2CO$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;

X is N, Y is $NR_2CO$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;

X is CH, Y is $NR_2CO$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$.

Preferred compounds are:

(S)—N—[8—Methyl-5-(4-methylpiperazin-1-yl)-3,4-dihydro-2H-1-benzopyran-3-yl]-4-(dimethylaminocarbonyl)benzamide and N—(4—Morpholinophenyl)-8-methoxy-5-(4-methylpiperazin-1-yl)-3,4-dihydro-2H-1-benzopyran-3-carboxamide The compounds of the present invention are in the form of the racemate or the (R)- or (S)-enantiomer in the form of a free base or a pharmaceutically acceptable salt or solvate thereof. Compounds in the form of the (S)-enantiomer are considered preferred.

Both organic and inorganic acids can be employed to form non-toxic pharmaceutically acceptable acid addition salts of the compounds of this invention. Illustrative acids are sulfuric, nitric, phosphoric, oxalic, hydrochloric, formic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. These salts are readily prepared by methods known in the art.

The preferred solvates of the compounds of this invention are the hydrates.

Pharmaceutical Formulations

In a second aspect the present invention provides a pharmaceutical formulation comprising as active ingredient a therapeutically effective amount of the compound of formula I as an enantiomer or a racemate in the form of a free base or a pharmaceutically acceptable salt or solvate thereof, optionally in association with diluents, excipients or inert carriers.

According to the present invention the compound of the invention will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or poly-ethylene glycol. Hard gelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01–100 mg/kg bodyweight at peroral administration and 0.001–100 mg/kg bodyweight at parenteral administration.

The compound of the invention may be used in a combination with a 5-HT reuptake inhibitor, such as fluoxetine, paroxetine, citalopram, clomipramine, sertraline, alaproclate or fluvoxamin, preferably paroxetine or citalopram. Another possible combination is to use the compound of the invention together with a monoamine oxidase inhibitor, such as moclobemide, tranylcypramine, brofaromide or phenelzine, preferably moclobemide or phenelzine. Still another possible combination is the compound of the invention together with a 5-HT$_{1A}$ antagonist, such as the compounds disclosed in WO 96/33710, preferably (R)-5-carbamoyl-3—(N,N-dicyclobutylamino)-8-fluoro-3,4-dihydro-2H-1-benzopyran.

Medical and Pharmaceutical Use

In a further aspect the present invention provides the use of the compounds of formula I in therapy as a h5-HT$_{1B}$ antagonist, partial agonist or full agonist, preferably as an antagonist and the use in the treatment of 5-hydroxytryptamine mediated disorders. Examples of such disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulation, pain and hypertension. Other examples of hydroxytryptamine mediated disorders are urinary incontinence, vasospasm and growth control of tumors (e g lung carcinoma).

Methods of Preparation

The present invention also relates to processes for preparing the compound of formula I. Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, Wiley-Interscience, New York, 1991.

Methods of Preparation of Intermediates

1. In the case where Y is NR$_2$CO and X is N (i) Benzylation of the compound of the formula II, either as a racemate (described in: Thorberg, S-O.; Hall, H.; Åkesson, C.; Svensson, K.; Nilsson, J. L. G. *Acta Pharm. Suec.* 1987, 24(4), 169–182) or as an enantiomer (described in: patent application WO 93/07135),

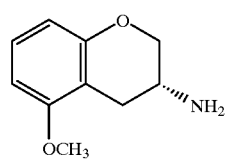

(II)

to obtain a compound of formula III by the reaction with a suitable benzylating agent, e.g. benzyl halide such as benzyl bromide, benzyl chloride, or an activated alcohol, e.g. benzyl-mesylate or tosylate. The reaction may be carried out by using the salt or the base of compound II in a suitable solvent, e.g. N,N-dimethylformamide, acetone or acetonitrile, with a suitable base, e.g. NaOH, NaHCO$_3$, K$_2$CO$_3$ or a trialkylamine, such as triethylamine at a reaction temperature within the range of +20° C. to +150° C. The presence of a suitable catalyst, e.g. alkali metal iodide such as potassium iodide or sodium iodide, may increase the speed of the reaction.

(ii) Demethylation of the compound of formula III

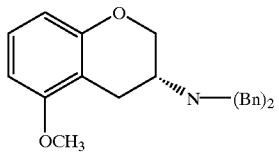
(III)

to obtain a compound of formula IV may be carried out by treating the compound with an acidic reagent such as aqueous HBr, HI, HBr/CH₃COOH, BBr₃, AlCl₃, pyridine—HCl or with a basic nucleophilic reagent such as CH₃C₆H₄SNa or C₂H₅SNa in a suitable solvent. Suitable solvents may be methylene chloride or chloroform and at a reaction temperature between −78° C. and +60° C.

(iii) Conversion of the compound of formula IV to a compound of formula V

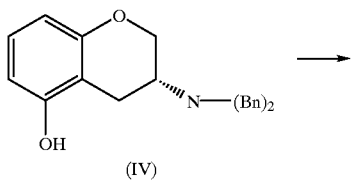
(IV)

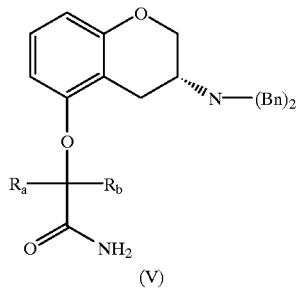
(V)

may be carried out by the reaction with a compound of formula VI

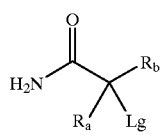
(VI)

where Lg denotes a leaving group, e.g. a halogen such as chlorine, bromine or iodine or an alkane- or arenesulfonyloxy group such as a p-toluenesulfonyloxy group, and $R_a$ and $R_b$ are hydrogen or a lower alkyl group, e.g. methyl. The process may be carried out with a salt of the compound of formula IV obtained by reaction with a base such as K₂CO₃, Na₂CO₃, KOH, NaOH, BuLi or NaH. The reaction may be conducted in a suitable solvent, e.g. an aprotic solvent such as dioxane, N,N-dimethylformamide, tetrahydrofuran, toluene, benzene or petroleum ether, and the reaction may occur between +20° C. and +150° C.

(iv) Rearrangement of a compound of formula V to a compound of formula VII

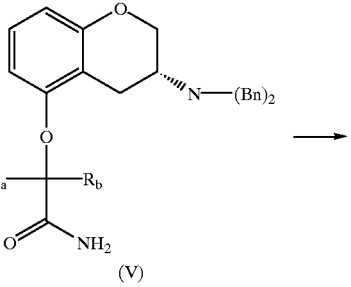
(V)

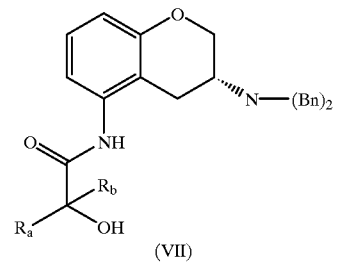
(VII)

may be carried out in a suitable solvent, e.g. aprotic solvent such as N,N dimethylformamide, dioxane, 1,1,3,3-tetramethylurea, tetrahydrofuran or hexamethylphosphoric triamide, with a suitable base, e.g. K₂CO₃, KOH, potassium tertbutoxide or NaH, at a reaction temperature within the range of +20° C. to +150° C. The presence of a co-solvent such as 1,3-dimethyl-3,4,5,6-tetrahydro-2(1H)-pyrimidone or hexamethylphosphoric triamide in appropriate concentration in the solvent may increase the speed of the reaction.

(v) Hydrolysis of a compound of formula VII to a compound VIII may be carried out under acidic conditions using acids such as H₂SO₄, HCl or HBr in a suitable solvent, e.g. H₂O, ethanol, methanol or mixtures thereof, and the reaction may occur between +20° C. and +100° C. or under basic conditions using bases such as NaOH or KOH in a suitable solvent, e.g. H₂O, ethanol, methanol or mixtures thereof, and at a reaction temperature between +20° C. and +100° C.

(vi) Conversion of compound of formula VIII to a compound of formula IX

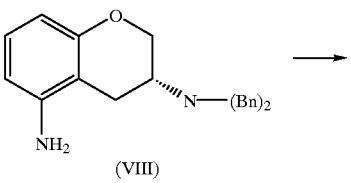
(VIII)

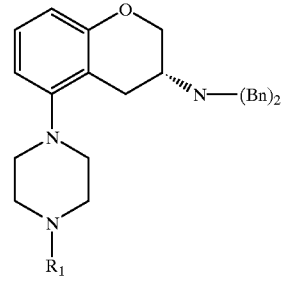
(IX)

may be carried out by a) reaction with a compound of formula X

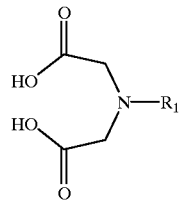

(X)

where $R_1$ is $C_1$–$C_6$ alkyl or $C_3$–$C_6$ cycloalkyl. The process may be carried out in a suitable solvent, e.g. an aprotic/anhydrous solvent such as tetrahydrofuran or N,N-dimethylformamide, in the presence of coupling reagent such as N,N-carbonyldiimidazole and the reaction may occur between +20° C. and +130° C. The reaction is followed by the reduction of the imide with a suitable reducing agent, e.g. $LiAlH_4$, in a suitable solvent, e.g. diethyl ether or tetrahydrofuran, at a temperature between +20° C. and reflux, or b) by reaction with a compound of formula XI

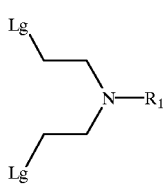

(XI)

where Lg denotes a leaving group, e.g. a halogen such as chlorine, bromine or iodine, or an alkane- or arenesulfonyloxy group such as p-toluenesulfonyloxy group, and $R_1$ is $C_1$–$C_6$-alkyl or $C_3$–$C_6$ cycloalkyl. The process may be carried out in a suitable solvent such as ethanol, butanol, N,N-dimethylformamide, acetonitrile or a mixture of water and acetonitrile with a suitable base, e.g. $K_2CO_3$, $NaHCO_3$ or KOH, and at a reaction temperature between +20° C. and +150° C.

(vii) Halogenation of the compound of formula IX to a compound of formula XII where $R_c$ denotes bromine, chlorine or iodine may be performed by a reagent such as ICl or $Br_2$, $Cl_2$ or $SO_2Cl_2$ with or without a suitable base such as sodium acetate in a suitable solvent such as acetic acid at a reaction temperature between +20° C. and +50° C.

(viii) The conversion of a compound of formula XII where $R_c$ is a halogen, e.g. bromine or iodine, to a compound of formula XIII where $R_1$ is $C_1$–$C_6$ alkyl or $C_3$–$C_6$ cycloalkyl and $R_e$ is $C_1$–$C_6$ alkyl

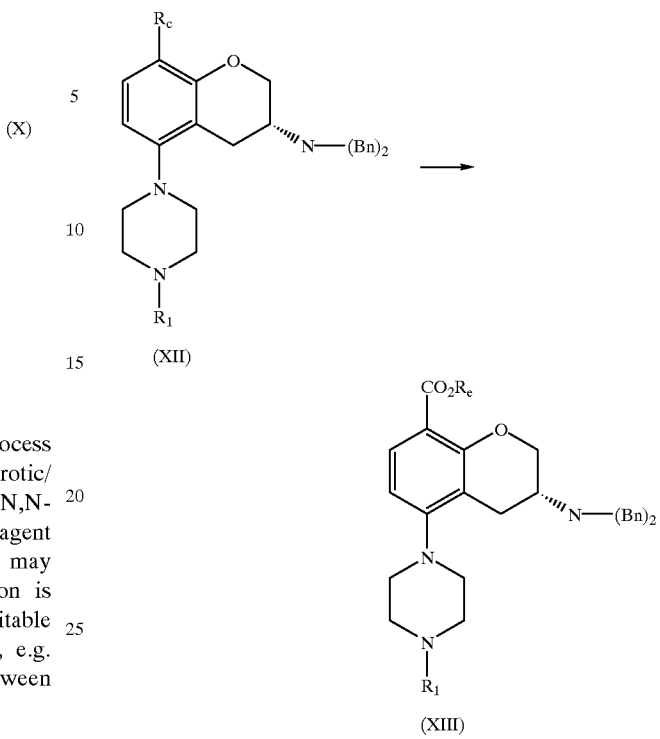

may be carried out by palladium-catalysed carbonylation. The process may be performed by reacting XII with an alcohol of formula $R_eOH$ where $R_e$ is $C_1$–$C_6$ alkyl at atmospheric or at elevated carbon monoxide pressure in a suitable solvent such as dioxane or N,N-dimethylformamide and at a reaction temperature between +20° C. and +120° C. in the presence of a suitable catalyst such as $PdX_2$, $L_2Pd(O)$, $L_2PdX_2$ where X denotes a halogen such as chlorine or bromine or for acetate and L denotes a suitable ligand such as triphenylphosphine, 1,3-bis(diphenylphosphinopropane) or 1,1'-bis(diphenylphosphino)ferrocene and a suitable trialkylamine such as triethylamine.

(ix) Conversion of a compound of formula XIII to a compound of formula XIV where $R_1$ is $C_1$–$C_6$ alkyl or $C_3$–$C_6$ cycloalkyl and $R_9$ is $CONR_6R_7$ wherein $R_6$ and $R_7$ are H, $C_1$–$C_6$ alkyl or $C_3$–$C_6$ cycloalkyl may be performed by, a) hydrolysis under basic conditions with a suitable base such as KOH, LiOH or $C_2H_5SNa$ in a suitable solvent such as methanol, tetrahydrofuran or N,N-dimethylformamide, in the presence of water at a reaction temperature between 20° C. and reflux temperature, or under acidic conditions in a suitable solvent such as methanol or ethanol using acids such as aqueous HBr, HI, $HBr/CH_3COOH$ at a reaction temperature between 20° C. and reflux temperature, or cleavage with a Lewis acid such as $BBr_3$ or TMSI in a suitable solvent such as methylene chloride or chloroform and at a reaction temperature between −78° C. and +120° C.

b) conversion of the above formed acid to a acid chloride with a suitable reagent such as $SOCl_2$ or $(COCl)_2$, neat or in a suitable solvent such as methylene chloride or chloroform with or without a catalytic amount of N,N-dimethylformamide at a reaction temperature between −20° C. and reflux temperature.

c) reacting the acid chloride with an excess of an amine of formula $NHR_6R_7$ where $R_6$ and $R_7$ are H, $C_1$–$C_6$ alkyl or $C_3$–$C_6$ cycloalkyl in a suitable solvent such as methylene chloride or dioxane at a reaction temperature between −20° C. and reflux temperature.

(x) Conversion of a compound of formula XIII to a compound of formula XV where $R_1$ is $C_1$–$C_6$ alkyl or $C_3$–$C_6$ cycloalkyl may be performed by reduction with a suitable reducing agent such as $LiAlH_4$ or $LiAlH_2(OCH_2CH_2OCH_3)_2$ in a suitable solvent such as diethyl ether, tetrahydrofuran or toluene at a reaction temperature between +20° C. and reflux temperature.

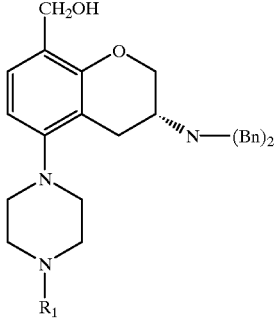

(XV)

(xi) Conversion of a compound of formula XIV where $R_9$ is $CONR_6R_7$ and $R_6$ and $R_7$ are H, $C_1$–$C_6$ or $C_3$–$C_6$ cycloalkyl to a compound of formula XVI where $R_1$ is $C_1$–$C_6$ alkyl or $C_3$–$C_6$ cycloalkyl and $R_9$ is CN or $CONR_6R_7$ where $R_6$, $R_7$ are H, $C_1$–$C_6$ alkyl or $C_3$–$C_6$ cycloalkyl

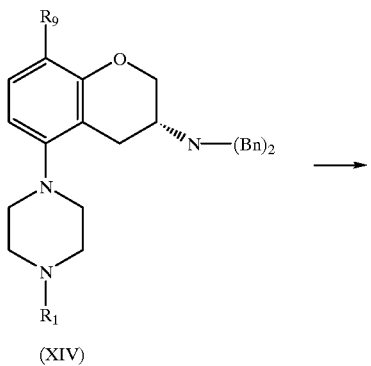

(XIV)

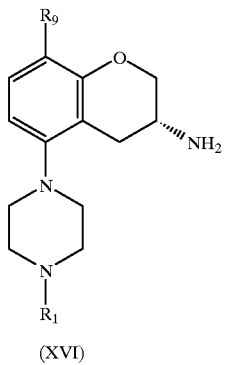

(XVI)

may be carried out by cleavage of the benzyl groups by hydrogenation over a suitable catalyst containing palladium, rhodium, platina or nickel in a suitable solvent, e.g. acetic acid or ethanol, and the reaction may occur between +20° C. and +120° C. or, by debenzylation using ammonium formate and palladium on carbon in a suitable solvent such as methanol at a reaction temperature between +20° C. and +65° C.

Conversion of a compound of formula XIV where $R_9$ is $CONH_2$ to a compound of formula XVI where $R_9$ is CN may be performed by
a) debenzylation as described above followed by,
b) dehydration with a suitable reagent such as $SOCl_2$ or $P_2O_5$ in a suitable solvent such as methylene chloride or toluene at a reaction temperature between +20° C. and +110° C.

(xii) Conversion of a compound of formula XV to a compound of formula XVI where $R_1$ is $C_1$–$C_6$ alkyl or $C_3$–$C_6$ cycloalkyl and $R_9$ is methyl may be performed by cleavage of the benzyl groups and reduction of the benzyl alcohol under conditions described in method xi above in a suitable solvent such as acetic acid with or without a strong acid such as HCl or HBr.

(xiii) Conversion of a compound of formula XII to a compound of formula XVII where $R_1$ is $C_1$–$C_6$ alkyl or $C_3$–$C_6$ cycloalkyl and $R_9$ is OH

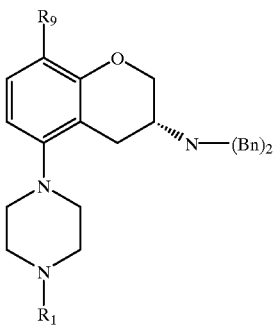

(XVII)

may be performed by metal-halogen exchange using a suitable alkyllithium or metal such as n-butyllithium or lithium in a suitable solvent such as tetrahydrofuran or diethyl ether, followed by treatment with trimethylborate, a peroxy acid such as peracetic acid or hydrogen peroxide and an acid such as acetic acid. The reaction may be performed at a temperature between −78° C. and +20° C.

(xiv) Conversion of a compound of the formula XII to a compound of the formula XVII where $R_9$ is $C_1$–$C_6$ alkyl or $C_3$–$C_6$ cycloalkyl or fluorine may be performed by lithium-halogen exchange using a suitable alkyllithium or metal such as n-butyllithium or lithium in a suitable solvent such as tetrahydrofuran or diethyl ether, followed by treatment with an alkyl halide such as methyl iodide or ethyl iodide or by a fluorinating agent such as N-fluorobenzenesulfonimide and at a reaction temperature between −78° C. and room temperature.

(xv) Conversion of a compound of formula XVII to a compound of formula XVI where $R_9$ is $C_1$–$C_6$ alkyl, $C_3$–$C_6$ cycloalkyl, F or OH may be performed by debenzylation under conditions described in method xi above.

(xvi) Conversion of a compound of formula XVII where $R_9$ is OH to a compound of formula XVI where $R_9$ is $C_1$–$C_6$ alkoxy or $OCHF_2$ may be performed by alkylation with a suitable alkylating agent such as an alkyl halide, e.g methyl iodide or ethyl iodide or chlorodifluoromethane, in the presence of a suitable base such as NaH, KOH or NaOH in a suitable solvent such as isopropanol, N,N-dimethylformamide or dioxane at a reaction temperature between +20° C. and +80° C. followed by debenzylation under conditions described in method xi above.

(xvii) Conversion of a compound of formula IX to a compound of formula XVI where $R_9$ is a halogen such as bromine, chlorine or iodine may be performed by debenzylation under conditions described in method xi above followed by halogenation using a suitable reagent such as $Br_2$, $Cl_2$, $SO_2Cl_2$ or $ICl$ in a suitable solvent such as acetic acid, HCl/ethanol, methylene chloride or toluene with or without a suitable base such as sodium acetate at a reaction temperature between $-20°$ C. and $+20°$ C.

(xviii) Conversion of a compound of formula XVI, to a compound of formula XVIII, where $R_1$ is $C_1$–$C_6$ alkyl or $C_3$–$C_6$ cycloalkyl, $R_2$ is H, $C_1$–$C_5$ alkyl and $R_9$ is as in formula I above, may be performed by

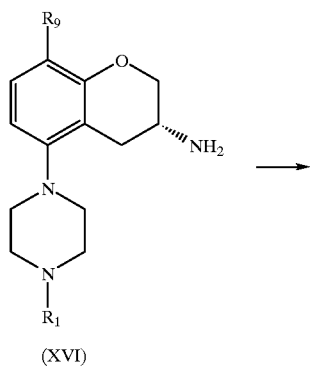

(XVI)

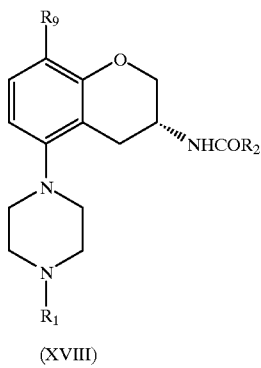

(XVIII)

acylation with an appropriate activated carboxylic acid of formula $R_2COOH$ where $R_2$ is H or $C_1$–$C_5$ alkyl in a suitable solvent such as methylene chloride or chloroform in the presence of a suitable base such as KOH, NaOH, $K_2CO_3$ or a trialkylamine e.g. triethylamine.

Activation of the carboxylic acid may be achieved by a) transforming the carboxylic acid into the corresponding acid chloride using a reagent such as $SOCl_2$ or $(COCl)_2$ in a suitable solvent such as methylene chloride or chloroform with or without a catalytic amount of N,N-dimethylformamide at a reaction temperature between $+20°$ C. and $+110°$ C.

(xix) Conversion of a compound of formula XVIII to a compound of formula XIX where $R_1$ is $C_1$–$C_6$ alkyl or $C_3$–$C_6$ cycloalkyl and $R_2$ is $C_1$–$C_6$ alkyl may be performed by reduction with a suitable reducing agent such as lithium aluminum hydride or diborane in a suitable solvent such as diethyl ether, tetrahydrofuran or dioxane at a reaction temperature between $+20°$ C. and reflux temperature.

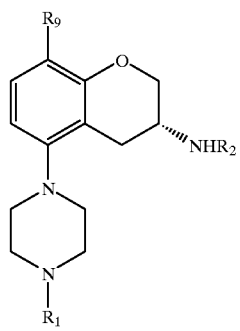

(XIX)

(xx) Conversion of a compound of formula VIII to a compound of formula XX may be performed with for example bis(2-chloroethyl)benzylamine or benzylaminodiacetic acid under conditions described in method vi above.

(xxi) Conversion of a compound of formula XX to a compound of formula XXI where $R_c$ is bromine, chlorine or iodine may be performed under conditions described in method vii above.

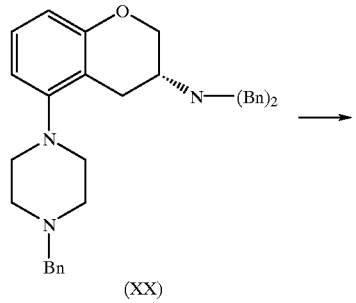

(XX)

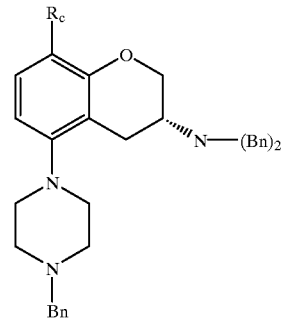

(XXI)

(xxii) Conversion of a compound of formula XXI to a compound of formula XXII where $R_9$ is a) $C_1$–$C_6$ alkyl or fluorine may be performed by litium-halogen exchange and reaction with an appropriate alkyl halide or a fluorinating agent under conditions described in method xiv above.

b) $CONR_6R_7$ wherein $R_6$ and $R_7$ are $C_1$–$C_6$ alkyl or $C_3$–$C_6$ cycloalkyl may be performed by reacting XXI with an excess of an amine of the formula $NHR_6R_7$ wherein $R_6$ and $R_7$ are as described above at atmospheric or elevated carbon monoxide-pressure using a suitable catalyst such as $L_2PdX_2$ where L denotes a suitable ligand such as triphenylphosphine or 1,1'-bis(diphenylphosphino)ferrocene and X denotes chlorine, bromine or acetate, in a suitable solvent such as N,N-dimethylformamide or dioxane and at a reaction temperature between $+20°$ C. and $+100°$ C.

(xxiii) Conversion of a compound of formula XXII to a compound of formula XXIII where $R_9$ is $C_1-C_6$ alkyl or fluorine and $R_d$ is a suitable protecting group such as tert-butyloxycarbonyl or benzoyloxycarbonyl may be performed by

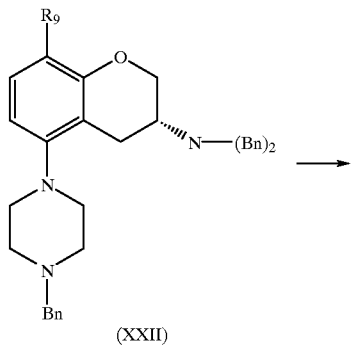

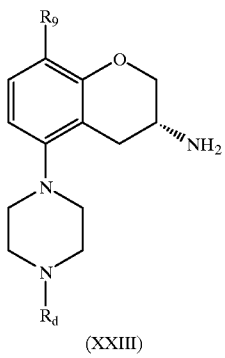

debenzylation under conditions described in method xi above followed by reaction with a suitable acylation agent such as di-tert-butylcarbonate and a suitable base such as triethylamine in a suitable solvent such as methylene chloride or chloroform and at a reaction temperature between 0° C. and +20° C.

(xxiv) Conversion of a compound of formula XX to a compound of formula XXIII where $R_9$ is a halogen such as bromine, chlorine or iodine may be performed by
a) debenzylation under conditions described in method xi above
b) halogenation under conditions described in method vii above
c) protection under conditions described in method xxiii above.

2. In the case where Y is $CONR_2$ and X is N (i) Conversion of a compound of formula XXV either as a racemate (described in: Thorberg, S-O.; Hall, H.; Åkesson, C.; Svensson, K.; Nilsson, J. L. G. *Acta Pharm. Suec.* 1987, 24(4), 169–182) or as an enantiomer to a compound formula XXVI

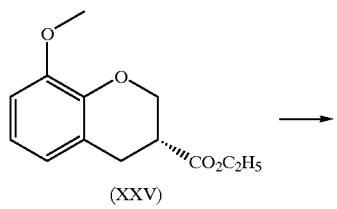

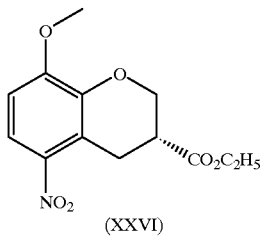

may be performed by electrophilic aromatic substitution using nitric acid in a suitable solvent such as acetic anhydride, methylene chloride or acetic acid at a reaction temperature between −20° C. and room temperature.

(ii) Conversion of a compound of formula XXVI, to a compound of formula XXVII, where $R_9$ is methoxy, may be performed by hydrolysis either under acidic conditions using acids such as $H_2SO_4$, HCl or HBr in a suitable solvent such as water, ethanol, methanol, acetic acid or mixtures thereof and the reaction may occur at temperatures between +20° C. and reflux or, under basic conditions using bases such as KOH, NaOH or LiOH in a suitable solvent such as water, ethanol, methanol or mixtures thereof and the reaction may occur at temperatures between +20° C. and reflux.

(iii) Conversion of a compound of formula XXVII to a compound of formula XXVIII where Y is $CONR_2$ wherein $R_2$ and $R_3$ is as defined in formula I above may be performed by

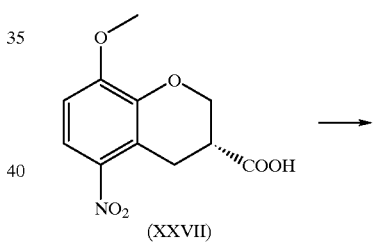

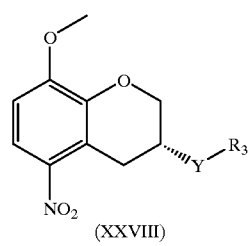

a) activating the carboxylic acid of formula XXVII under conditions described in method 1, xviii above
b) reacting the formed acid chloride with an amine of formula $NHR_2R_3$ where $R_2$ and $R_3$ are as defined in formula I above, in a suitable solvent such as methylene chloride or chloroform in the presence of a suitable base such as triethylamine or $K_2CO_3$ at a reaction temperature between −20° C. and reflux temperature.

(iv) Conversion of a compound of formula XXVIII to a compound of formula XXIX, where $R_9$ is $C_1-C_6$ alkyl, $C_1-C_6$ alkoxy, $CONR_6R_7$ where $R_6$ and $R_7$ are $C_1-C_6$ alkyl or $C_1-C_6$ cycloalkyl and Y is $CONR_2$ wherein $R_2$ and $R_3$ is as defined in formula I above, may be performed by

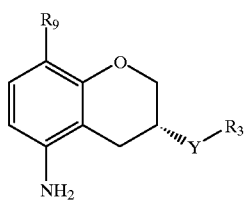

(XXIX)

reduction of the nitro group either using hydrogen at atmospheric or elevated pressure and a catalyst such as palladium, platina or nickel in a suitable solvent such as methanol, ethanol or acetic acid at a reaction temperature between +20° C. and +120° C. or by a reducing agent such as sodium dithionite or stannous chloride or ammonium formate and Pd/C in a suitable solvent such as methanol or ethanol at a reaction temperature between +20° C. and +80° C.

(v) Conversion of a compound of formula XXVI to a compound of formula XXX may be performed by demethylation under conditions described in method 1, ii above. During the demethylation of XXVI, cleavage of the ester may occur and the carboxylic acid could in such case be re-esterified by methods known by a person skilled in the art.

(vi) Conversion of a compound of formula XXX to a compound with formula XXXI where $R_e$ is $C_1$–$C_6$ alkyl may be performed by

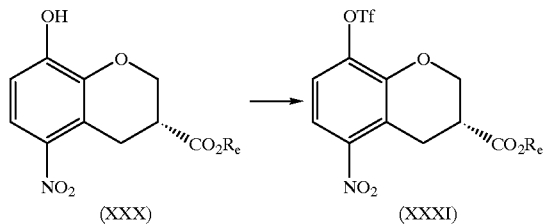

(XXX)    (XXXI)

reacting XXX with a reagent such as trifluoromethanesulfonic anhydride or N-(2-pyridyl)triflimide and a suitable base such as triethylamine or lithium diisopropylamide in a suitable solvent such as methylene chloride or tetrahydrofuran and at a reaction temperature between –78° C. and 0° C.

(vii) Conversion of a compound of formula XXXI, to a compound of formula XXVII where the carboxylic acid has a protection group $R_e$ and $R_9$ is a) $C_1$–$C_6$ alkyl, may be carried out by a Stille-coupling using an alkyltin reagent such as tetramethyltin and a suitable catalyst such as $L_2PdCl_2$ wherein L is a suitable ligand such as triphenylphosphine or 1,1'-bis(diphenylphosphino)ferrocene in the presence of LiCl in a suitable solvent such as N,N-dimethylformamide or dioxane at a reaction temperature between +20° C. and +100° C.

b) $CONR_6R_7$ wherein $R_6$ and $R_7$ are $C_1$–$C_6$ alkyl or $C_3$–$C_6$ cycloalkyl, may be performed by reacting XXXI with an excess of an amine of the formula $NHR_6R_7$ wherein $R_6$ and $R_7$ are as described above at atmospheric or elevated carbon monoxide-pressure using a suitable catalyst such as $L_2PdX_2$ where L denotes a suitable ligand such as triphenylphosphine or 1,1'-bis(diphenylphosphino)ferrocene and X denotes chlorine, bromine or acetate, in a suitable solvent such as N,N-dimethylformamide or dioxane and at a reaction temperature between +20° C. and +100° C.

(viii) Conversion of a compound of formula XXXI to a compound of formula XXXII may be performed by

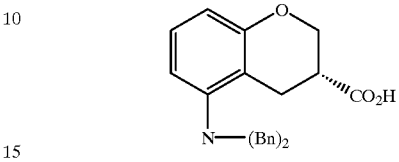

(XXXII)

a) reduction under conditions described in method 1, xi above b) benzylation under conditions described in method 1, i above c) hydrolysis of the ester under conditions described in method 1, ix above.

(ix) Conversion of a compound of formula XXXII to a compound of formula XXIX where $R_9$ is a halogen such as bromine, chlorine or iodine may be performed by a) activating the carboxylic acid under conditions described in method 1, xviii above b) reacting with an amine of formula $NHR_2R_3$ wherein $R_2$ is hydrogen or $C_1$–$C_6$alkyl, $R_3$ is $C_1$–$C_6$ alkyl, $C_3$–$C_6$ cycloalkyl or $(CH_2)_n$-aryl, wherein aryl is phenyl or a heterocyclic ring containing one or two heteroatoms selected from N,O and S and which may be mono- or disubstituted with $R_4$ and/or $R_5$;

wherein $R_4$ is hydrogen, $C_1$–$C_6$ alkyl, $C_3$–$C_6$ cycloalkyl, $C_1$–$C_6$ alkoxy, F, $CF_3$, OH, $SO_2NR_6R_7$, phenyl, phenyl—$C_1$–$C_6$ alkyl, phenoxy, $C_1$–$C_6$ alkylphenyl, an optionally substituted heterocyclic or heteroaromatic ring containing one or two heteroatoms selected from N, O, S, $SO_2$ wherein the substituent(s) is (are) selected from $C_1$–$C_6$ alkyl or $C_3$–$C_6$ cycloalkyl, phenyl—$C_1$–$C_6$ alkyl;

wherein $R_6$ and $R_7$ are hydrogen, $C_1$–$C_6$ alkyl or $C_3$–$C_6$ cycloalkyl;

wherein $R_5$ is hydrogen, OH, F, $CF_3$, $C_1$–$C_6$ alkyl or $C_3$–$C_6$ cycloalkyl;

and n is 0–4 c) debenzylation under conditions described in method 1, xi above d) halogenation under conditions described in method vii above.

3. In the case where Y is $NR_2CO$ and X is CH (i) Conversion of a compound of formula XXV to a compound of formula XXXIII may be performed by electrophilic aromatic substitution using a halogenating reagent such as $Br_2$ or N-bromosuccinimide and a suitable base such as sodium acetate in a suitable solvent such as acetic acid or acetonitrile and at a reaction temperature between 0° C. and +20° C.

(ii) Conversion of a compound of formula XXXIII to a compound of formula XXXIV may be performed by

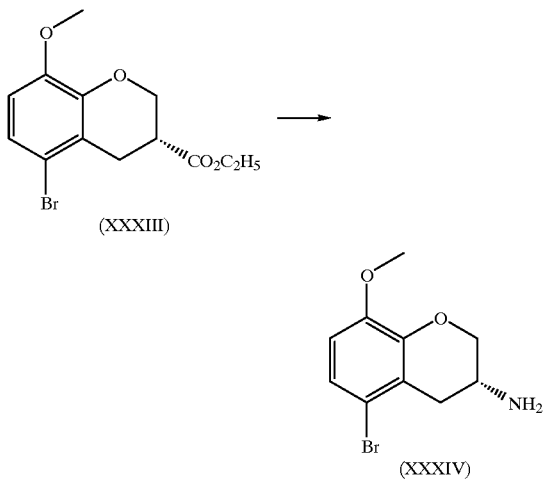

a) hydrolysis of the ester under conditions described in method 1, v above
b) a Curtius rearrangement by transforming the carboxylic acid into an acyl azide with a suitable reagent such as $SOCl_2$ and a suitable base such as triethylamine in a suitable solvent such as methylene chloride or toluene followed by heating the formed acid chloride with sodium azide or by reacting the carboxylic acid with diphenoxyphosphoryl azide in a suitable solvent such as methanol or water at reflux. If methanol is used as the solvent the formed carbamate may be hydrolysed to the amine under conditions described in method 1, v above.

(iii) Conversion of a compound of formula XXXIV to a compound of formula XXXV may be performed by benzylation under conditions described in method 1, i above.

(iv) Conversion of a compound of formula XXXV to a compound of formula XXXVI where $R_1$ is $C_1$–$C_6$ alkyl or $C_3$–$C_6$ cycloalkyl may be performed by

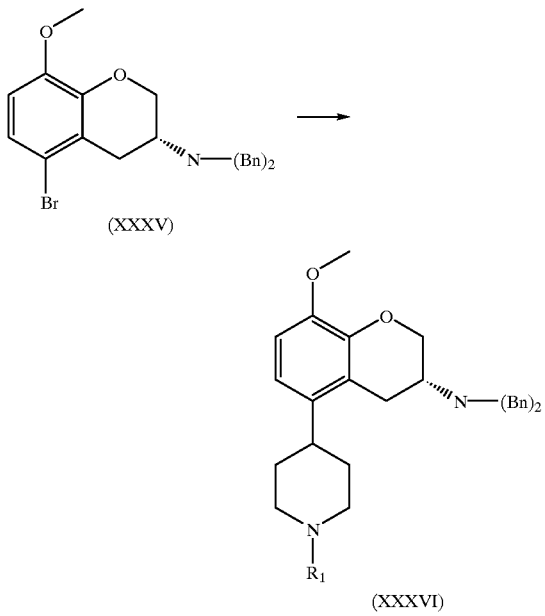

a) a halogen-metal exchange using an alkyllithium or a metal such as n-butyllithium, lithium or magnesium fol-lowed by treatment with an appropriate N-alkyl-4-piperidone such as N-methyl-4-piperidone in a suitable solvent such as tetrahydrofuran or diethyl ether at a reaction temperature between −78° C. and 0° C.
b) reduction of the formed benzylic alcohol by a suitable reducing agent such as sodium borohydride or triethylsilane and an acid such as $CF_3CO_2H$ or $CF_3SO_3H$ in a suitable solvent such as tetrahydrofuran or diethyl ether at a reaction temperature between 0° C. and +65° C.

(v) Conversion of a compound of formula XXXVI to a compound of formula XXXVII where $R_1$ is $C_1$–$C_6$ alkyl or $C_3$–$C_6$ cycloalkyl may be performed by
a) demethylation under conditions described in method 1, ii above
b) triflating the formed phenol under conditions described in method 2, xxx above.

(vi) Conversion of a compound of formula XXXVII to a compound of formula XXXVIII where $R_9$ is
a) $C_1$–$C_6$ alkyl, may be carried out by a Stille-coupling under conditions described in method 2, vii-a
b) $CONR_6R_7$ wherein $R_6$ and $R_7$ are $C_1$–$C_6$ alkyl or $C_3$–$C_6$ cycloalkyl may be performed by

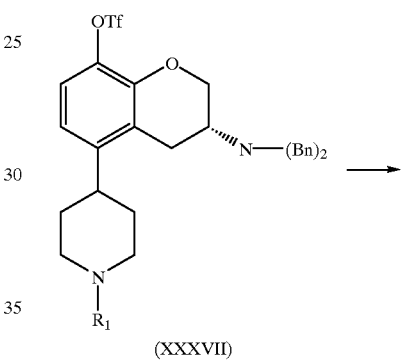

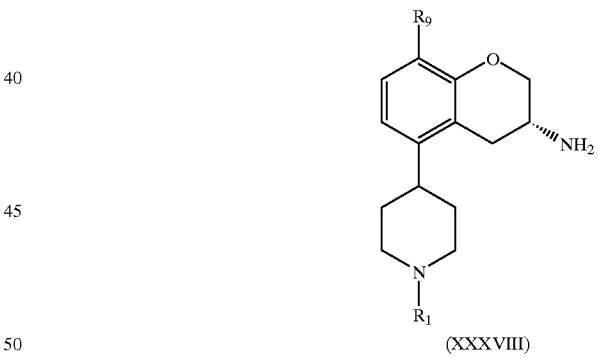

palladium-catalyzed carbonylation under conditions described in method 1, xxii-b.

(vii) Conversion of a compound of formula XXXVI to a compound of formula XXXVIII where $R_9$ is
a) methoxy, may be performed by debenzylation under conditions described in method 1, xi above
b) hydroxy, may be performed by demethylation under conditions described in method 1, ii above followed by debenzylation as described in method 1, xi above
c) $C_2$–$C_6$ alkoxy or $OCHF_2$, may be performed by demethylation as described in method 1, ii above followed by alkylation under conditions described in method 1, xvi and debenzylation as described in method 1, xi above.

(viii) Conversion of a compound of formula XXXVIII to a compound of formula XXXVIX where $R_9$ is $C_1$–$C_6$ alkyl, $C_1$–$C_6$ alkoxy, $OCHF_2$ or hydroxy and $R_2$ is $C_1$–$C_6$ alkyl may be performed by

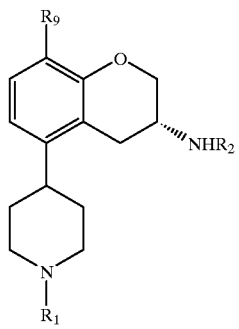

(XXXIX)

a) amidation of XXXVIII with a carboxylic acid of the formula $R_2CO_2H$ wherein $R_2$ is hydrogen or $C_1$–$C_5$ under conditions described in method 1, xviii above b) reduction under conditions described in method 1, xix above.

(ix) Conversion of a compound of formula XXXVII to a compound of formula XL where $R_1$ is $C_1$–$C_6$ alkyl or $C_3$–$C_6$ cycloalkyl and $R_e$ is $C_1$–$C_6$ alkyl may be performed under conditions described in method 1, viii above.

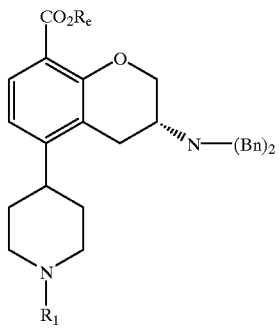

(XL)

(x) Conversion of a compound of formula XL to a compound of formula XXXVIII where $R_1$ is $C_1$–$C_6$ alkyl or $C_3$–$C_6$ cycloalkyl and $R_9$ is CN may be performed by a) amidation with $NH_3$ under conditions described in method 1, ix above b) dehydration of the primary amide and debenzylation under conditions described in method 1, xi above.

Method of Preparation of End Products

Another object of the invention is a process A(i), A(ii), A(iii), B(i), B(ii), C(i), C(ii), D or E for the preparation of the compound of general formula I by A(i)

acylation, in the case where $R_1$ is $C_1$–$C_6$ alkyl or $C_3$–$C_6$ cycloalkyl, Y is $NR_2CO$, $R_2$ is hydrogen and X, $R_3$ and $R_9$ are as defined in general formula I above, of a compound of formula A

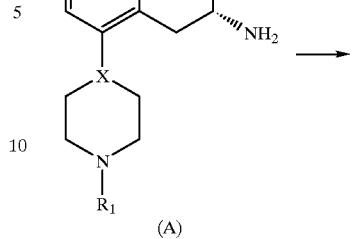

(A)

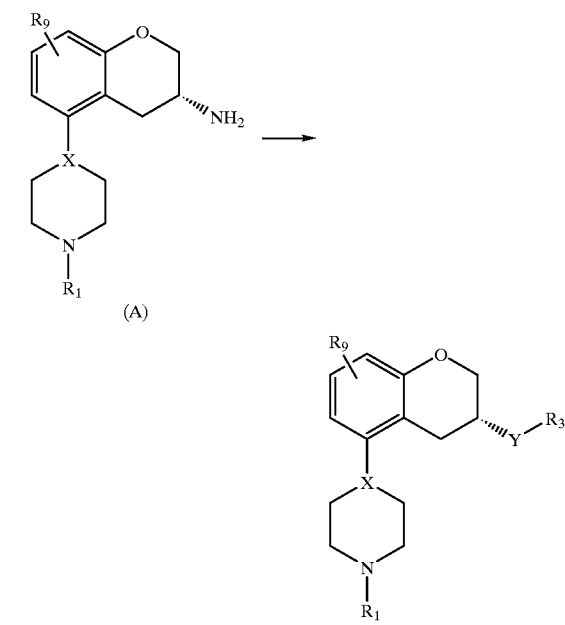

(I)

with an activated carboxylic acid $R_3$—$COLg_1$ where $Lg_1$ is a leaving group or by using a carboxylic acid $R_3$—COOH with an activating reagent.

Thus, the acylation according to the process A(i) may be carried out with an appropriate activated carboxylic acid, $R_3COLg_1$ where $R_3$ is as defined above and $Lg_1$ is a leaving group, such as halogen, e.g. chlorine, in a suitable solvent such as methylene chloride or chloroform with a suitable base, e.g. a trialkylamine such as triethylamine, at a temperature between −20° C. and reflux temperature or by using an carboxylic acid, $R_3COOH$ wherein $R_3$ is as defined above with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C.

Method A (ii)

acylation, in the case where $R_1$ is $C_1$–$C_6$ alkyl or $C_3$–$C_6$ cycloalkyl, Y is $NR_2CO$, $R_2$ is $C_1$–$C_6$ alkyl and X, $R_3$ and $R_9$ are as defined in general formula I above, of a compound of formula B,

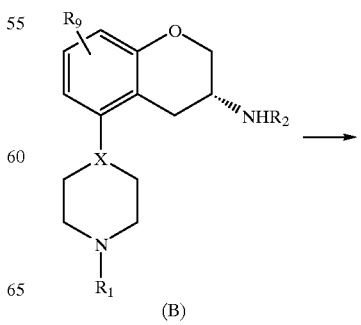

(B)

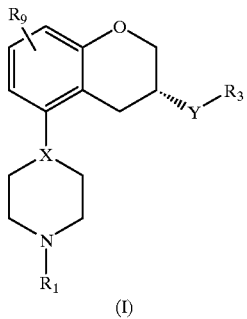

(I)

with an activated carboxylic acid $R_3$—$COLg_1$ where $Lg_1$ is a leaving group or by using a carboxylic acid $R_3$—$COOH$ with an activating reagent.

Thus, the acylation according to the process A(ii) may be carried out with an appropriate activated carboxylic acid, $R_3COLg_1$ where $R_3$ is as defined above and $Lg_1$ is a leaving group, such as halogen, e.g. chlorine, in a suitable solvent such as methylene chloride or chloroform with a suitable base, e.g. trialkylamine such as triethylamine at a temperature between −20° C. and reflux temperature or by using an carboxylic acid, $R_3COOH$ wherein $R_3$ is as defined above with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C.

Method A (iii)

acylation, in the case where $R_1$ and $R_2$ are hydrogen, Y is $NR_2CO$, $R_d$ is a protecting group and X, $R_3$ and $R_9$ are as defined in general formula I above, of a compound of formula C

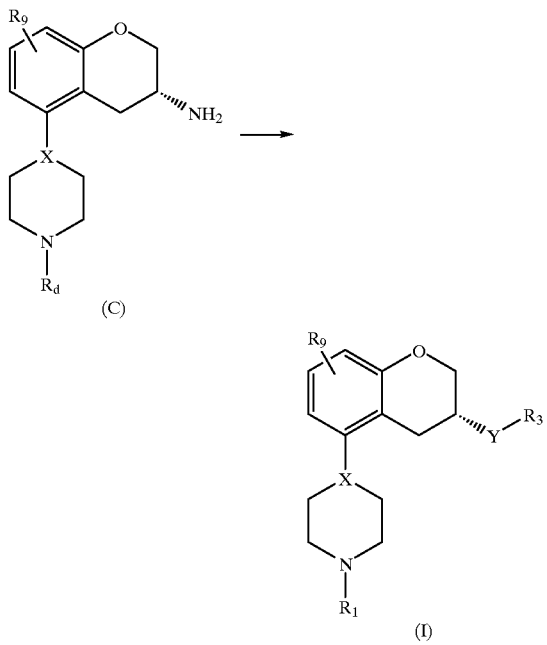

with an activated carboxylic acid $R_3$—$COLg_1$ where $Lg_1$ is a leaving group or by using a carboxylic acid $R_3$—$COOH$ with an activating reagent, followed by the removal of the protecting group $R_d$;

Thus, the acylation according to the process A(iii) may be carried out with an appropriate activated carboxylic acid, $R_3COLg_1$ where $R_3$ is as defined above and $Lg_1$ is a leaving group, such as halogen, e.g. chlorine, in a suitable solvent such as methylene chloride or chloroform with a suitable base, e.g. trialkylamine such as triethylamine, or by using a carboxylic acid, $R_3COOH$ where $R_3$ is defined as above, with an activating reagent, e.g. N,N'-carbonyldiimidazole, N,N'-dicyclohexylcarbodiimide or diphenylphosphinic chloride, with a suitable base such as N-methylmorpholine in a suitable solvent such as N,N-dimethylformamide or tetrahydrofuran and the reaction may be conducted at a temperature between +20° C. and +150° C., followed by removal of the protecting group $R_d$ by hydrolysis in a suitable solvent such as methylene chloride or chloroform with a suitable acid such as trifluoroacetic acid at a temperature between +20° C. and +60° C.

Method B (i)

reacting, in the case where Y is $CONR_2$, $R_2$, $R_3$ and $R_9$ is as defined in general formula I above, a compound of formula D

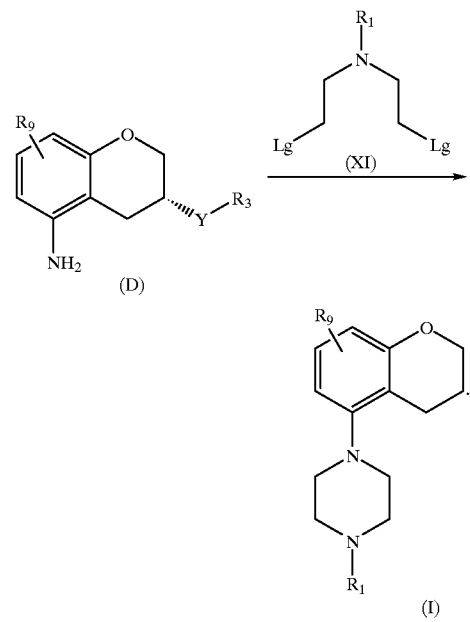

with a compound of formula XI wherein Lg is a leaving group.

Thus, the reaction according to the process B(i) may be carried out with a compound of formula XI wherein $R_1$ is as defined in general formula I and Lg is a leaving group, e.g. a halogen such as chlorine, bromine or iodine, or an alkane- or arenesulfonyloxy group such as p-toluenesulfonyloxy group. The process may be carried out in a suitable solvent such as ethanol, butanol, N,N-dimethylformamide, acetonitrile or a mixture of water and acetonitrile with or without a suitable base, e.g. $K_2CO_3$, $NaHCO_3$ or KOH, and the reaction may occur between +20° C. and +150° C.

Method B (ii)

reacting, in the case where Y is $CONR_2$, $R_1$ is H, $R_2$, $R_3$ and $R_9$ is as defined in general formula I above with the exception of when $R_4$ and $R_9$ are substituents that are susceptible to catalytic hydrogenation known by a person skilled in the art, a compound of formula D

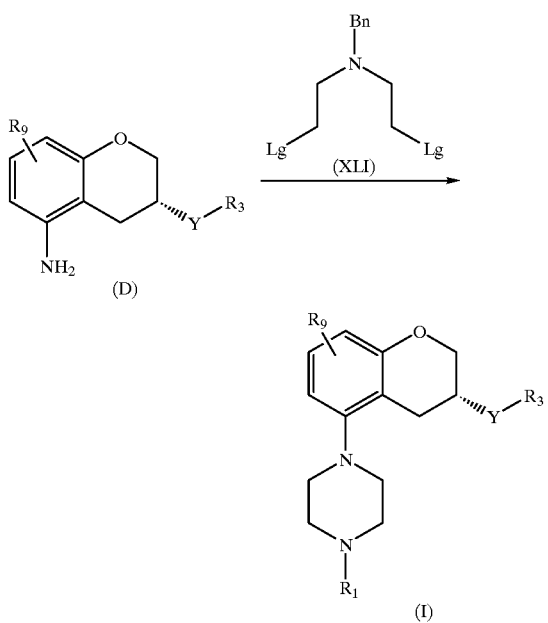

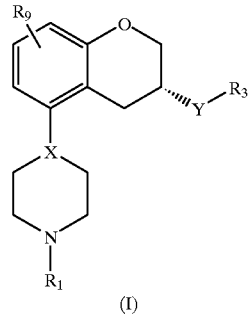

with a compound of formula XLI wherein Lg is a leaving group.

Thus, the reaction according to the process B(ii) may be carried out with a compound of formula XLI where Lg is a leaving group, e.g. a halogen such as chlorine, bromine or iodine, or an alkane- or arenesulfonyloxy group such as p-toluenesulfonyloxy group. The process may be carried out in a suitable solvent such as ethanol, butanol, N,N-dimethylformamide, acetonitrile or a mixture of water and acetonitrile with or without a suitable base, e.g. $K_2CO_3$, $NaHCO_3$ or KOH, and the reaction may occur between $+20°$ C. and $+150°$ C. followed by removal of the benzyl group by catalytic hydrogenation at atmospheric or elevated pressure using a catalyst such as palladium, platina or nickel in a suitable solvent such as methanol, ethanol or acetic acid with or without an acid such as HCl or HBr at a reaction temperature between $+20°$ C. and $+100°$ C.

Method C (i)

reacting, in the case where Y is $NR_2SO_2$, $R_2$ is hydrogen, $R_1$, $R_3$ and $R_9$ is as defined in general formula I above, a compound of formula E

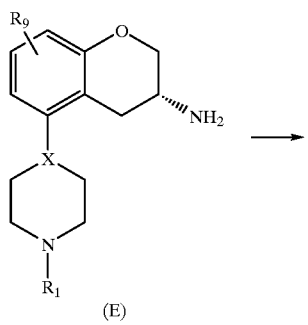

with an appropriate activated sulfonic acid $R_3SO_2Lg_1$, where $Lg_1$ is a leaving group such as a halogen, e.g. chlorine, in a suitable solvent such as methylene chloride or chloroform with a suitable base, e.g. a trialkylamine such as triethylamine, and the reaction may be conducted at a temperature between $-20°$ C. and $+60°$ C.

Method C (ii)

reacting, in the case where Y is $NR_2SO_2$, $R_2$ is $C_1$–$C_6$ alkyl, $R_1$, $R_3$ and $R_9$ is as defined in general formula I above, a compound of formula E

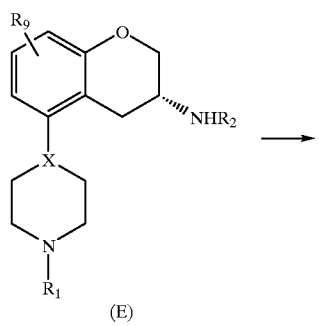

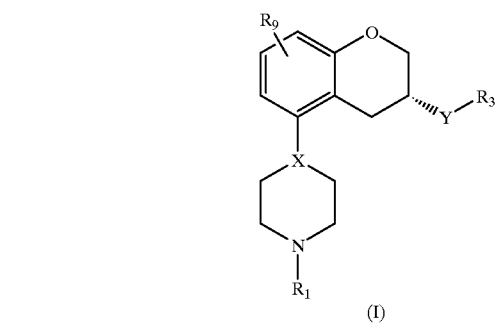

with an appropriate activated sulfonic acid $R_3SO_2Lg_1$, where $Lg_1$ is a leaving group such as a halogen, e.g. chlorine, in a suitable solvent such as methylene chloride or chloroform with a suitable base, e.g. trialkylamine such as triethylamine, and the reaction may be conducted at a temperature between $-20°$ C. and $+60°$ C.

Method D reduction, where Y is $NR_2CH_2$ or $CH_2NR_2$, and X, $R_1$, $R_2$, $R_3$ and $R_9$ are as in formula I above with the exception of when $R_4$ and $R_9$ are substituents that are susceptible to certain reducing agents known by a person skilled in the art, of a compound of formula I above where Y is $NR_2CO$ or $CONR_2$, and X, $R_1$, $R_2$, $R_3$ and $R_9$ are as in formula I above,

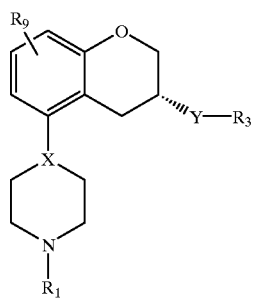

(I)

may be carried out with an appropriate reducing agent such as lithium aluminum hydride, borane or borane-dimethylsulfide in a suitable solvent, e.g. diethyl ether, dioxan or tetrahydrofuran, at a temperature between +20° C. and reflux temperature.

Method E alkylation, in the case where $R_1$ is $C_1$–$C_6$ alkyl or $C_3$–$C_6$ cycloalkyl, Y is $NR_2CH_2$ and X, $R_2$ $R_3$ and $R_9$ are as defined in general formula I above with the exception of when $R_4$ and $R_9$ are substituents that are susceptible to certain alkylations known by a person skilled in the art, of a compound of formula B,

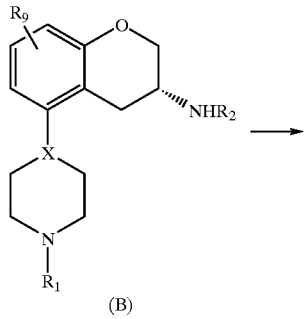

(B)

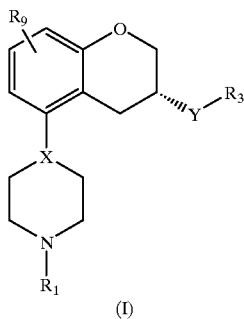

(I)

may be carried out with an appropriate alkylating agent.

Thus, alkylation may be carried out with an alkylating reagent of formula $R_3Lg$ where Lg is a leaving group, such as a halogen, e.g. chlorine, bromine or iodine, or an alkane- or arenesulfonyloxy group, such as p-toluenesulfonyloxy group, in the presence of a base such as triethylamine or $K_2CO_3$ and the reaction may be performed in a suitable solvent such as acetonitrile or N,N-dimethylformamide and at a reaction temperature between +20° C. and +100° C. or by reductive alkylation with an aldehyde of formula $R_3CHO$ and a reducing agent such as sodium cyanoborohydride in a suitable solvent such as methanol or tetrahydrofuran or a mixture thereof and adjustment of pH to slightly acidic by an acid such as acetic acid and the reaction may be performed at a temperature between +10° C. to +50° C.

Intermediates

The present invention also refers to new intermediates, namely intermediates of formulas

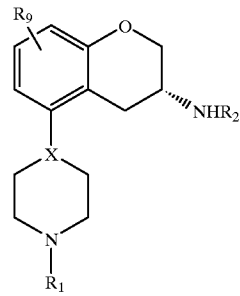

wherein X is N or CH;

$R_1$ is $C_1$–$C_6$ alkyl or $C_3$–$C_6$ cycloalkyl;

$R_2$ is hydrogen or $C_1$–$C_6$ alkyl;

$R_9$ is $C_1$–$C_6$ alkyl, $C_3$–$C_6$ cycloalkyl, $OCF_3$, $OCHF_2$, $OCH_2F$, halogen, CN, $CF_3$, OH, $C_1$–$C_6$ alkoxy, $C_1$–$C_6$ alkoxy—$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl; or $COR_8$; wherein $R_6$ is H, $C_1$–$C_6$ alkyl or $C_3$–$C_6$ cycloalkyl;

$R_7$ is H, $C_1$–$C_6$ alkyl or $C_3$–$C_6$ cycloalkyl; and $R_8$ is $C_1$–$C_6$ alkyl, $C_3$–$C_6$ cycloalkyl, $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$ wherein $R_6$ and $R_7$ are as defined above;

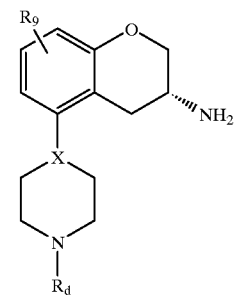

wherein

X is N;

$R_9$ is as defined above;

$R_d$ is a protecting group;

and

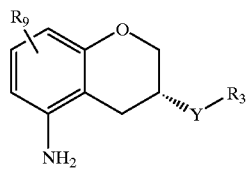

wherein
Y is $CONR_2$;
$R_2$ is hydrogen or $C_1$–$C_6$ alkyl;
$R_3$ is as defined above; and
$R_9$ is as defined above.

The invention is illustrated but not restricted to the following working examples.

Working Examples

Example 1
(S)-3—N,N—Dibenzylamino-5-methoxy-3,4-dihydro-2H-1-benzopyran Hydrochloride (S)-3—Amino-5-methoxy-3,4-dihydro-2H-1-benzopyran (45 g, 0.25 mol; described in: WO 93/07135), $K_2CO_3$ (120 g, 0.87 mol) and benzylbromide (65 mL, 0.55 mol) were mixed in acetonitrile (1000 mL) under nitrogen. The reaction mixture was refluxed for 45 h. The mixture was filtered and the solvent was removed in vacuo, and the residue was partitioned between diethyl ether and saturated NaCl (aq). The layers were separated and the organic phase was dried ($MgSO_4$) and filtered followed by precipitation of the hydrochloric salt at room temperature. Yield: 99 gram (99%). An analytical sample was transferred to the base: $[\alpha]^{21}_D$+116° (c 1.0, chloroform). EIMS (70eV) m/z (relative intensity) 359 (28, M+).

Example 2
(S)-3—N,N—Dibenzylamino-5-hydroxy-3,4-dihydro-2N-1-benzopyran (S)-3—N,N—Dibenzylamino-5-methoxy-3,4-dihydro-2H-1-benzopyran hydrochloride (67 g, 0.17 mol) was dissolved in methylene chloride (500 mL) under nitrogen, and the solution was cooled to −75° C. Boron tribromide (32 mL, 0.34 mol) was added dropwise over 5 min. The temperature was then allowed to slowly reach +5° C., and the reaction was stirred overnight. The reaction mixture was carefully quenched with an 2 M aqueous solution of $NH_3$ under stirring. The layers were separated and the aqueous phase was extracted two times with methylene chloride. The organic layers were combined, washed with brine, dried ($MgSO_4$), filtered and the solvent was removed in vacuo to give a brownish oily residue which was purified by flash chromatography on a silica gel column using methylene chloride as the eluent. Yield: 50 g (86%) of the title compound: $[\alpha]^{21}_D$+109° (c 1.0, chloroform); EIMS (70eV) m/z (relative intensity) 345 (5, M+).

Example 3
(S)-2-(3—N,N-Dibenzylamino-3,4-dihydro-2H-1-benzopyran-5-yloxy)-2-methylpropanamide (S)-3—N,N-Dibenzylamino-5-hydroxy-3,4-dihydro-2H-1-benzopyran (50 g, 0.14 mol) was dissolved in anhydrous 1,4-dioxane (450 mL) under nitrogen. A dispersion of sodium hydride (60–65% in oil, 6.1 g, 0.15 mol) was added in portions. The mixture was stirred for 1 h at room temperature. 2—Bromo-2-methylpropanamide (24 g, 0.14 mol; Coutts, I. G. C.; Southcott, M. R. *J. Chem. Soc. Perkin Trans.* 1 1990, 767–771) was added to the dark greenish solution and was heated at reflux with stirring for 3 h. An additional amount of sodium hydride (60–65% in oil, 2.8 g, 70 mmol) and 2-bromo-2-methylpropanamide (4.6 g, 28 mmol) was added in portions and heating at 60° C. was continued for 17 h. After cooling, a small amount of methanol (10 mL) was added and the solution was filtered and the solvent was removed in vacuo. The residue was partitioned between ethyl acetate (500 mL) and a saturated $NaHCO_3$ solution (50 mL). The organic layer was dried ($MgSO_4$), and the solvent was removed in vacuo to give a brownish residue which was crystallized from ethyl acetate/hexane. Yield: 45 g (71%) of the title compound as a white solid: mp 133–134° C.; $[\alpha]^{21}_D$+99° (c 1.0, chloroform).; EIMS (70eV) m/z (relative intensity) 430 (9, M+).

Example 4
(S)-5—Amino-3—N,N-dibenzylamino-3,4-dihydro-2H-1-benzopyran

To a solution of (S)-2-(3—N,N-dibenzylamino-3,4-dihydro-2H-1-benzopyran-5-yloxy)-2-methylpropanamide (46 g, 0.11 mol) in anhydrous N,N-dimethylformamide (450 mL) and 1,3-dimethyl-3,4,5,6-tetrahydro-2(1H)-pyrimidinone (45 mL) was added sodium hydride (60–65% in oil, 8.5 g, 0.21 mol) in portions under nitrogen. The reaction mixture was heated at 110° C. with stirring for 13 h. The mixture was then allowed to cool, and the solution was partitioned between ethyl acetate (400 mL) and a 2 M $NH_3$ solution (200 mL). The layers were separated, and the aqueous layer was extracted with ethyl acetate (150 mL). The combined organic layers were dried ($MgSO_4$) and concentrated in vacuo to give a brownish oil. EIMS (70eV) m/z (relative intensity) 430 (3, M+).

The obtained material (0.11 mol) was dissolved in ethanol (350 mL). A 6 M HCl solution (250 mL) was added, and the reaction mixture was heated at reflux for 16 h. After stirring, the mixture was allowed to cool to 35° C., the ethanolic solvent was removed in vacuo, and ethyl acetate was added to the aqueous remains. The mixture was cooled on ice, and a solution of conc. $NH_3$ was slowly added with stirring. The layers were separated, and the aqueous layer was extracted with another portion of ethyl acetate. The combined organic layers were dried ($MgSO_4$), and the solvent was removed in vacuo to give a brownish oil which was purified on a short column of silica gel (eluent: hexane/ethyl acetate; 8:2) affording 25 g (68% yield) of the desired compound as a light yellow oil. The product slowly crystallized upon standing in the refrigerator. An analytical sample was recrystallized from diethyl ether/petroleum ether: mp 101–103° C.; $[\alpha]^{21}_D$+123° (c 1.0, chloroform); EIMS (70eV) m/z (relative intensity) 344 (17, M+).

Example 5
(S)-1-(3—N,N—Dibenzylamino-3,4-dihydro-2H-1-benzopyran-5-yl)-4-methylpiperazine-2,6-dione To a dispersion of N-methyliminodiacetic acid (6.90 g, 46.9 mmol) in anhydrous tetrahydrofuran (575 mL) was added 1,1'-carbonyldiimidazole (15.2 g, 93.9 mmol), and the mixture was heated at reflux for 2 h under nitrogen. A solution of (S)-5-amino-3—N,N-dibenzylamino-3,4-dihydro-2H-1-benzopyran (15.0 g, 42.7 mmol) in tetrahydrofuran (120 mL) was added with stirring over 0.5 h. The reaction mixture was heated at reflux for 28 h, then allowed to cool, and the solvent was removed in vacuo. The residue was purified on a short column of silica gel (eluent: methylene chloride and ethyl acetate) affording 14.1 g (71% yield) of the title compound as a light yellow solid: mp sinters>60° C.; $[\alpha]^{21}_D$+89° (c 1.0, chloroform); EIMS (70eV) m/z (relative intensity) 455 (8, M+).

Example 6
(S)-3—N,N—Dibenzylamino-5-(4-methylpiperazin-1-yl)-3,4-dihydro-2-1-benzopyran To a stirred solution of (S)-1-(3—N,N-dibenzylamino-3,4-dihydro-2H-1-benzopyran-5-yl)-4-methylpiperazine-2,6-dione (25.4 g, 55.8 mmol) in anhydrous diethyl ether (800 mL) was added lithium aluminum hydride (9.30 g, 246 mmol) in portions. The reaction mixture was heated to reflux for 6.5 h under nitrogen and was stirred overnight at room temperature. The mixture was cooled (ice-bath), and water (10 mL) was added followed by a 15% aqueous solution of NaOH (10 mL) and another portion of water (30 mL). The precipitate was filtered off and washed with several portions of warm tetrahydrofuran. The organic layers were combined, and the solvent was removed in vacuo. The residue was purified by column chromatography on silica (eluent: chloroform/ethanol; 95:5+0.5% conc. $NH_3$) affording 13.6 g (57% yield) of the title compound as a light yellow oil: $[\alpha]^{25}_D$+63° (c 1.0, methanol); EIMS (70eV) m/z (relative intensity) 427 (5, M+).

Example 7
(S)-3—N,N—Dibenzylamino-8-iodo-5-(4-methylpiperazin-1-yl)-3,4-dihydro-2H-1-benzopyran (S)-3—N,N—Dibenzylamino-5-(4-methylpiperazin-1-yl)-3,4-dihydro-2H-1-benzo-1-pyran (6.9 g, 16 mmol) and sodium acetate (1.5 g, 18 mmol) were dissolved in acetic acid (430 mL). To the solution was added iodine monochloride (18 mL, 1 M, 18 mmol) and the reaction mixture was stirred at room temperature, while protected from light, for 24 h. Additional iodine monochloride (2.5 mL, 1 M, 2.5 mmol) was added followed by stirring for 3 h. The solvent was evaporated in vacuo and the residue was partitioned between methylene chloride (800 mL) and 2 M NaOH (120 mL). The aqueous phase was extracted with methylene chloride (100 mL) and the combined organic layers were washed with brine (2×100 mL) and dried ($MgSO_4$). Evaporation of the solvent gave 8.6 g of a crude product. Purification by column chromatography on silica using ethyl acetate/ethanol (saturated with ammonia) (25:1) as the eluent gave 4.1 g (43% yield) of the title compound (containing about 7% of the starting material) as a yellowish solid: EIMS (70eV) m/z (relative intensity) 553 (15, M+). The product was used in the next step without further attempts to purification.

Example 8
(S)-8—Methoxycarbonyl-3—N,N-dibenzylamino-5-(4-methylpiperazin-1-yl)-3,4-dihydro-2H-1-benzopyran (S)-3—N,N—Dibenzylamino-8-iodo-5-(4-methylpiperazin-1-yl)-3,4-dihydro-2H-1-benzopyran (2.6 g, 4.8 mmol) was dissolved in N,N-dimethylformamide (100 mL) and flushed with carbon monoxide. To the solution was added palladium acetate (110 mg, 0.48 mmol), 1,3-bis(diphenylphosphino)propane (200 mg, 0.48 mmol), methanol (25 mL) and triethylamine (3.3 mL, 24 mmol). The mixture was reacted with carbon monoxide at 90° C. and at atmospheric pressure for 8 h. The solution was filtered, the solvent was evaporated. The residue was co-evaporated with xylene (2×50 mL) and partitioned between methylene chloride (300 mL) and 2 M $NH_3$ (50 mL). The aqueous phase was extracted with methylene chloride (50 mL) and the combined organic layers were washed with brine (2×50 mL) and dried (MgSO4). The solvent was evaporated giving 4.0 g of a crude product. Purification by column chromatography on silica using methylene chloride/ethanol is (saturated with ammonia) (50:1) as the eluent gave 1.7 g (68% yield) of the title compound (containing about 5% of the corresponding 8—H analogue) as a yellowish solid: EIMS (70 eV) m/z (relative intensity) 485 (8, M+). The product was used in the next step without further attempts to purification.

Example 9
(S)-3—N,N—Dibenzylamino-8-hydroxymethyl-5-(4-methylpiperazin-1-yl)-3,4-dihydro-2H-1-benzopyran (S)-8—Methoxycarbonyl-3—N,N-dibenzylamino-5-(methylpiperazin-1-yl)-3,4-dihydro-2H-1-benzopyran (490 mg, 1.0 mmol) was dissolved in dry tetrahydrofuran (40 mL) and lithium aluminium hydride (76 mg, 2.0 mmol) was added portionwise. The reaction mixture was stirred at 45° C. for 4 h and cooled to room temperature. The reaction was quenched by the addition of water (76µL), 15% NaOH (76µL) and water (225µL) and stirred for 18h. The white precipitate was filtered off and the solution was dried ($MgSO_4$). The solvent was evaporated in vacuo giving 520 mg of a crude product. Purification by column chromatography on silica using chloroform/ethanol (saturated with ammonia) (15:1) as the eluent gave 390 mg (85% yield) of the title compound containing about 8% of the corresponding 8-methyl analogue as a yellowish oil: EIMS (70eV) m/z (relative intensity) 457 (15, M+).

Example 10
(S)-3—Amino-8-methyl-5-(4-methylpiperazin-1-yl)-3,4-dihydro-2H-1-benzopyran (S)-3—N,N—Dibenzylamino-8-hydroxymethyl-5-(4-methylpiperazin-1-yl)-3,4-dihydro-2H-1-benzopyran (420 mg, 0.90 mmol) was dissolved in methanol (60 mL) and ammonium formate (460 mg, 7.3 mmol) was added. The solution was flushed with nitrogen and palladium on carbon (120 mg, 10%) was added. The reaction mixture was stirred at 50° C. for 16 h. The catalyst was filtered off and the solvent was evaporated in vacuo giving 260 mg of a crude product. The residue was dissolved in acetic acid (50 mL) and palladium on carbon (120 mg, 10%) was added. The reaction mixture was hydrogenated at room temperature and at atmospheric pressure for 46 h. The catalyst was filtered off and the solvent was evaporated in vacuo. The residue was partitioned between ethyl acetate (120 mL) and 2 M NaOH (10 mL) and the aqueous phase was extracted with ethyl acetate (10 mL). The combined organic layers were washed with brine (5 mL), dried ($MgSO_4$) and the solvent was evaporated in vacuo giving 200 mg of a crude product. Purification by preparative TLC on silica using chloroform/ethanol (saturated with ammonia) (10:1) as the eluent afforded 150 mg (64% yield) of the title compound as an oil: EIMS (70eV) m/z (relative intensity) 261 (100, M+).

Example 11
(S)—N-[8—Methyl-5-(4-methylpiperazin-1-yl)-3,4-dihydro-2H-1-benzopyran-3-yl]-4-methylbenzamide 4—Methylbenzoic acid (22 mg, 0.16 mmol) and 1,1'-carbonyldiimidazole (27 mg, 0.17 mmol) were dissolved in dry N,N-dimethylformamide (2 mL) and stirred at 75° C. for 1 h. The reaction mixture was cooled to room temperature and a solution of (S)-3-amino-8-methyl-5-(methylpiperazin-1-yl)-3,4-dihydro-2H-1-benzopyran (40 mg, 0.15 mmol) dissolved in dry N,N-dimethylformamide (4 mL) was added. The reaction mixture was stirred at room temperature for 4 days and the solvent was evaporated in vacuo. The crude material was partitioned between methylene chloride (40 mL) and water (10 mL). The organic phase was washed with water (10 mL) and brine (5 mL) and dried ($MgSO_4$). The solvent was evaporated in vacuo giving 48 mg of a crude product. Purification by preparative TLC on silica using chloroform/ethanol (saturated with ammonia) (15:1) as the eluent afforded 23 mg (40% yield) of the title compound as a white solid: mp 191–192° C.; EIMS (70eV) m/z (relative intensity) 379 (100, M+); $[\alpha]^{21}_D$−7° (c 0.10, chloroform).

Example 12
(S)-8—Carbamoyl-3—N,N-dibenzylamino-5-(4-methylpiperazin-1-yl)-3,4-dihydro-2H-1-benzopyran (S)-8—Methoxycarbonyl-3—N,N-dibenzylamino-5-(4-methylpiperazin-1-yl)-3,4-dihydro-2H-1-benzopyran (800 mg, 1.6 mmol) and potassium hydroxide (500 mg, 8.9 mmol) were dissolved in methanol (50 mL) and stirred at 65° C. for 3 days. The solvent was evaporated in vacuo and the residue was co-evaporated with toluene (2×100 mL) giving 1.2 g of a crude material. The solid was dispersed in methylene chloride (40 mL) and thionyl chloride (1.2 mL, 16 mml) was added. The reaction mixture was heated to reflux for 1 h followed by evaporation of the solvent and excess thionyl chloride in vacuo. The residue was co-evaporated with toluene (100 mL) and dried in vacuo. The crude acid chloride was mixed with methylene chloride (40 mL) and cooled on ice. Concentrated ammonia (5 mL, 65 mmol) was added and the reaction mixture was stirred at about 0° C. for 20 min and at room temperature for 40 min. Methylene chloride (100 mL) and water (50 mL) were added and the aqueous layer was extracted with methylene chloride (30 mL). The combined organic layers were washed with brine (30 mL), dried (MgSO$_4$) followed by evaporation of the solvent in vacuo giving 790 mg of a crude product. Purification by preparative TLC on silica using chloroform/ethanol (saturated with ammonia) (15:1) as the eluent gave 460 mg (59% yield) of the title compound as white crystals: mp 173–174° C.; EIMS (70eV) m/z (relative intensity) 470 (4, M+).

Example 13
(S)-3—Amino-8-carbamoyl-5-(4-methylpiperazin-1-yl)-3,4-dihydro-2H-1-benzopyran (S)-8—Carbamoyl-3—N,N-dibenzylamino-5-(4-methylpiperazin-1-yl)-3,4-dihydro-2H-1-benzopyran (120mg mg, 0.95 mmol) was dissolved in methanol (40 mL) and palladium on carbon (480 mg, 10%) was added. The flask was flushed with nitrogen, ammonium formate (480 mg, 7.6 mmol) was added and the reaction mixture was stirred at 50° C. for 18 h. The catalyst was filtered off and the solvent was evaporated in vacuo. The residue was co-evaporated with toluene and dried in vacuo giving 300 mg (100% yield) of the title compound: EIMS (70eV) m/z (relative intensity) 290 (100, M+). The crude product was used in the next step without attempts to purification.

Example 14
(S)—N-[8—Carbamoyl-5-(4-methylpiperazin-1-yl)-3,4-dihydro-2H-1-benzopyran-3-yl]-4-benzoylbenzamide 4—Benzoylbenzoic acid (95 mg, 0.42 mmol) and 1,1'-carbonyldiimidazole (71 mg, 0.44 mmol) were dissolved in N,N-dimethylformamide (2 mL) and stirred at 75° C. for 1 h. The reaction mixture was cooled to room temperature and a solution of (S)-2-amino-8-carbamoyl-5-(4-methylpiperazin-1-yl)-3,4-dihydro-2H-1-benzopyran (120 mg, 0.40 mmol) in N,N-dimethylformamide (5 mL) was added. The reaction mixture was stirred at room temperature for 4 days and the solvent was evaporated in vacuo giving 290 mg of a crude product. Purification by preparative TLC on silica using chloroform/ethanol (saturated with ammonia) (15:1) as the eluent afforded 75 mg (38% yield) of the title compound: mp 259° C. (dec); EIMS (70eV) m/z (relative intensity) 498 (38, M+); $[\alpha]^{21}_D$-3° (c 0.1, chloroform).

Example 15
(S)—N-[8—Methyl-5-(4-methylpiperazin-1-yl)-3,4-dihydro-2H-1-benzopyran-3-yl]-4-(dimethylaminocarbonyl)benzamide 4—(Dimethylaminocarbonyl)benzoic acid (described in: Jurewicz, A. T; U.S. Pat. No. 3,607,918, 1971) (38 mg, 0.20 mmol) and 1,1'-carbonyldiimidazole (34 mg , 0.21 mmol) were dissolved in dry N,N-dimethylformamide (4 mL) and stirred at 75° C. for 1.5 h. The reaction mixture was cooled to room temperature and a solution of (S)-3-amino-8-methyl-5-(4-methylpiperazin-1-yl)-3,4-dihydro-2H-1-benzopyran (49 mg, 0.19 mmol) in dry N,N-dimethylformamide (5 mL) was added. The reaction mixture was stirred at 50° C. for 14 h and the solvent was evaporated in vacuo giving 120 mg of a crude product. Purification by preparative TLC using chloroform/methanol/conc. NH$_3$ (95:5:0.5) as the eluent afforded 40 mg (48% yield) of the title compound as a white foam: EIMS (70eV) m/z (relative intensity) 436 (26, M+); $[\alpha]^{21}_D$-9° (c 0.20, chloroform).

Example 16
8—Methoxy-5-nitro-3,4-dihydro-2H-1-benzopyran-3-carboxylic acid ethyl ester To a stirred solution of 8-methoxy-3,4-dihydro-2H-1-benzopyran-3-carboxylic acid ethyl ester (described in Thorberg, S-O et al. *Acta Pharm. Suec.*1987, 24, (4), 169–182) (5.5 g, 23 mmol) in methylene chloride (50 mL) at 0° C. was added dropwise 65% HNO$_3$ (2.0 mL). The solution was stirred at room temperature for 2 h and washed with water. The organic phase was dried and the solvent evaporated in vacuo. The residue was treated with diisopropyl ether (30 mL) and ethyl acetate (5 mL) to yield 1.5 g (5.3 mmol) of crystals of the 6-nitro isomer. The mother liquor was purified by column chromatography using diisopropylether as the eluent affording 1.3 g (20% yield) of the title compound: mp 66–68° C.; EIMS (70eV) m/z (relative intensity) 281 (100, M+).

Example 17
8—Methoxy-5-nitro-3,4-dihydro-2H-1-benzopyran-3-carboxylic acid

A mixture of 8-methoxy-5-nitro-3,4-dihydro-2H-1-benzopyran-3-carboxylic acid ethyl ester (5.8 g, 21 mmol) in ethanol (150 mL) and 2 M NaOH (15 mL) was heated to reflux for 30 min. The solvent was evaporated in vacuo the residue dissolved in water. Acidification to pH 2 and extraction with ethyl acetate followed by evaporation of the solvent in vacuo gave 4.9 g (94% yield) of the title compound: mp 181–183° C.; EIMS (70 eV) m/z (relative intensity) 253 (55, M+).

Example 18
N-(4—Morpholinophenyl)-8-methoxy-5-nitro-3,4-dihydro-2H-1-benzopyran-3-carboxamide To a solution of 8-methoxy-5-nitro-3,4-dihydro-2H-1-benzopyran-3-carboxylic acid (2.5 g, 10 mmol) in toluene (40 mL) and N,N-dimethylformamide (1 mL) was added thionyl chloride (3.6 mL, 50 mmol). The reaction mixture was refluxed for 2 h and the solvent was removed in vacuo. The residual acid chloride was added to a solution of 4-(1-morpholino)aniline (described in Devlin, J. P. et. al.,*J. Chem. Soc. Perkin Trans,* 1. 1975 830–841) (1.78 g, 10 mmol) and triethylamine (2.0 g, 20 mmol) in methylene chloride (30 mL) and stirred at 0° C. for 10 min and for 1 h at room temperature. The solvent was removed in vacuo and the residue was dissolved in ethyl acetate and washed with 2 M NaOH. Evaporation of the solvent in vacuo afforded 1.5 g (36% yield) of the title compound as white crystals: mp 238–240° C.; EIMS (70eV) m/z (relative intensity) 413 (5, M+).

Example 19
N-(4—Morpholinophenyl)-5-amino-8-methoxy-3,4-dihydro-2H-1-benzopyran-3-carboxamide To a solution of N-(4-morpholinophenyl)-8-methoxy-5-nitro-3,4-dihydro-2H-1-benzopyran-3-carboxamide (1.2 g, 2.9 mmol) in N,N-dimethylformamide (10 mL) was added a solution of sodium dithionite (2.1 g, 12 mmol) in water (5 mL). The mixture was stirred at 55° C. for 3 h and the solvent was removed in vacuo. The residue was purified by column chromatography on silica gel using ethyl acetate as the eluent affording 273 mg of the title compound (55% yield): EIMS (70eV) m/z (relative intensity) 383 (100, M+).

Example 20

N-(4—Morpholinophenyl)-8-methoxy-5-(4-methylpiperazin-1-yl)-3,4-dihydro-2H-1-benzopyran-3-carboxamide A solution of N-(4-morpholinophenyl)-5-amino-8-methoxy-3,4-dihydro-2H-1-benzopyran-3-carboxamide (270 mg, 0.7 mmol), bis (2-chloroethyl)-methylamine hydrochloride (288 g, 1.5 mmol) and sodium hydrogen carbonate (126 mg, 1.5 mmol) in n-butanol (10 mL) as stirred at 90° C. for 2.5 h. 2 M ammonia (10 mL) was added at 50° C., the mixture was cooled and the phases were separated. The organic phase evaporated in vacuo and the residue was purified by column chromatography on silica gel using ethyl acetate/triethyl amine (100:8) as the eluent affording 170 mg (50% yield) of the title compound as white crystals: mp 202–204° C.; EIMS (70eV) m/z (relative intensity) 466 (100 M+).

PHARMACOLOGY

Electrical field stimulation of [$^3$H]-5-HT release from occipital cortex of guinea pigs

[$^3$H]-5-HT is released by electrical field stimulation from slices of occipital cortex of guinea pigs which have been pre-incubated with [$^3$H]-5-HT. This release is similar to that caused by nerve stimulation, i.e. exocytotic release from serotonergic nerve terminals, depending on the presence of $Ca^{2+}$ in the incubation medium. The 5-HT release is regulated at the level of the nerve terminals by autoreceptors, in the guinea pigs (like in humans) belonging to the h5-$HT_{1B}$ receptor subtype. Thus, agonists of h5-$HT_{1B}$ receptors reduce the amount of [$^3$H]-5-HT released by electrical field stimulation whereas the release is increased by antagonists of this receptor type. Testing compounds with this method is accordingly a convenient screening technique for determining the potency and functional effect of new h5-$HT_{1B}$ receptor agonists and antagonists.

Methods and Materials

Buffer Composition (mM)

$NaHCO_3$ (25), $NaH_2PO_4.H_2O$ (1.2), NaCl (117), KCl(6), $MgSO_4 \times 7H_2O$ (1.2), $CaCl_2$(1.3), EDTA $Na_2$(0.03). The buffer is gassed for at least 30 min before use. The pH of the buffer is about 7.2 in the room temperature but it rises to about 7.4 at 37° C.

Preparation of Occipital Cortical Slices

Guinea pigs (200–250 g) were decapitated and the whole brain was removed. The occipital cortex was dissected and cut to slices 0.4×4 mm with McIlwain chopper machine. The white part of the tissue should be removed carefully with a tweezer before slicing. The slices were incubated in 5 ml buffer in the presence of 5 mM pargy line chloride. After incubation with 0.1 mM [$^3$H]-5-HT for another 30 min the slices were transferred to a test tube and washed three times with same volume buffer. The slices were transferred to the superfusion chambers with a plastic pipette and were washed for 40 min with the buffer in the presence of uptake inhibitor citalopram 2.5 μM with a flow 0.5 ml/min.

Electrical Stimulation of 5-HT Release

The superfused buffer was collected in 2 mL/fraction. The slices were stimulated by electricity with a train of pulses of frequency 3 Hz, duration 2 ms and current 30 mA for 3 min at the 4th and 13th fractions. The tested drugs were added from the 8th fraction to the end of experiment.

Results

A first electrical (or $K^+$) stimulation results in a standard amount of [$^3$H] 5-HT released ($S_1$). Between the first and the second stimulation the h5-$HT_{1B}$ antagonist is added to the media which results in a dose depending increase of the release($S_2$) after the second stimulation. See FIG. 1.

The $S_2/S_1$ ratio which is the per cent of released [$^3$H] 5-HT at the second stimulation ($S_2$) divided by that of the first stimulation ($S_1$) was used to estimate drug effects on transmitter release.

What is claimed is:

1. A compound of the formula I

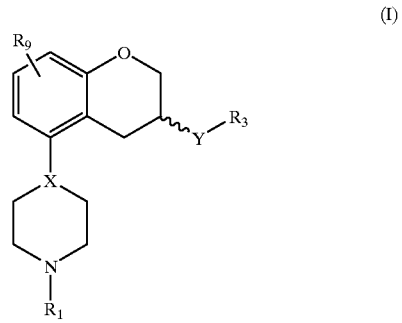

wherein

X is N or CH;

Y is $CH_2$—$NR_2$, $NR_2$—CO, CO—$NR_2$ or $NR_2SO_2$ wherein $R_2$ is H or $C_1$–$C_6$ alkyl;

$R_1$ is H, $C_1$–$C_6$, alkyl or $C_3$–$C_6$ cycloalkyl;

$R_3$ is $C_1$–$C_6$ alkyl, $C_3$–$C_6$ cycloalkyl or $(CH_2)_n$-aromatic ring, wherein the aromatic ring is phenyl or a heteroaromatic ring containing one or two heteroatoms selected from the soup consisting of N, O and S and wherein the aromatic ring may be mono- or di-substituted with $R_4$ and/or $R_5$;

wherein $R_4$ is H, $C_1$–$C_6$ alkyl, $C_3$–$C_6$ cycloalkyl, halogen, CN, $CF_3$, OH, $C_1$–$C_6$ alkoxy, $NR_6R_7$, $OCF_3$, $SO_3CH_3$, $SO_3CF_3$, $SO_2NR_6R_7$, phenyl, phenyl—$C_1$–$C_6$ alkyl, phenoxy, $C_1$–$C_6$ alkylphenyl, an optionally substituted heterocyclic or heteroaromatic ring containing one or two heteroatoms selected from N, O, S, SO and $SO_2$ wherein the substituent(s) is(are) selected from the group consisting of $C_1$–$C_6$ alkyl, $C_3$–$C_6$ cycloalkyl and phenyl—$C_1$–$C_6$ alkyl; or $COR_8$;

wherein $R_6$ is H, $C_1$–$C_6$ alkyl or $C_3$–$C_6$ cycloalkyl;

$R_7$ is H, $C_1$–$C_6$ alkyl or $C_3$–$C_6$ cycloalkyl; and $R_8$ is $C_1$–$C_6$ alkyl, $C_3$–$C_6$ cycloalkyl, $CF_3$, $NR_6R_7$, phenyl, or a heterocyclic ring containing one or two heteroatoms, selected from the group consisting of N O, S, SO and $SO_2$;

wherein $R_5$ is H, OH, $CF_3$, $OCF_3$, halogen, $C_1$–$C_6$ alkyl or $C_1$–$C_6$ alkoxy;

n is 0–4;

$R_9$ is $C_1$–$C_6$ alkyl, $C_3$–$C_6$ cycloalkyl, $OCF_3$, $OCHF_2$, $OCH_2F$, halogen, $CONR_6R_7$, CN, CF3, OH, $C_1$–$C_6$ alkoxy, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl, or $COR_8$;

wherein $R_6$, $R_7$ and $R_8$ are as defined above, wherein the compound is an (R)-enantiomer, an (S)-enantiomer, or a racemate in the form of a free base or a pharmaceutically acceptable salt or solvate thereof.

2. The compound according to claim 1 wherein Y is $NR_2CO$ or $CONR_2$.

3. The compound according to claim 1 wherein X is N.

4. The compound according to claim 1 wherein $R_1$ is H or $C_1$–$C_6$ alkyl.

5. The compound according to claim 1 wherein $R_3$ is $(CH_2)_n$-aromatic ring.

6. A compound according to claim 5 wherein the aromatic ring of substituent $R_3$ is substituted with $R_4$, and $R_4$ is an optionally substituted heterocyclic or heteroaromatic ring containing one or two heteroatoms selected from the group consisting of N, O and S; or $COR_8$.

7. The compound according to claim 5 or 6 wherein n is 0.

8. The compound according to claim 6 wherein $R_8$ is $NR_6R_7$ or a heterocyclic ring containing two heteroatoms selected from N and O.

9. The compound according to claim 1 wherein $R_9$ is $C_1$–$C_6$ alkyl, $OCHF_2$, halogen or $C_1$–$C_6$ alkoxy.

10. The compound according to claim 1 herein X is N, Y is $NR_2CO$ and $R_9$ is $C_1$–$C_6$ alkoxy.

11. The compound according to claim 6 wherein X is N, Y is $NR_2CO$, $R_4$ is morpholino or $COR_8$ and $R_9$ is $C_1$–$C_6$ alkoxy.

12. The compound according to claim 1 wherein X is N, Y is $NR_2CO$ and $R_9$ is $C_1$–$C_6$ alkyl.

13. The compound according to claim 6 wherein X is N, Y is $NR_2CO$, $R_4$ is morpholino or $COR_8$ and $R_9$ is $C_1$–$C_6$ alkyl.

14. The compound according to claim 1 wherein X is N, Y is $CONR_2$ and $R_9$ is $C_1$–$C_6$ alkoxy.

15. The compound according to claim 6 wherein X is N, Y is $CONR_2$, $R_4$ is morpholino or $COR_8$ and $R_9$ is $C_1$–$C_6$ alkoxy.

16. The compound according to claim 1 wherein X is N, Y is $CONR_2$ and $R_9$ is $C_1$–$C_6$ alkyl.

17. The compound according to claim 6 wherein X is N, Y is $CONR_2$, $R_4$ is morpholino or $COR_8$ and $R_9$ is $C_1$–$C_6$ alkyl.

18. A compound according to claim 1, wherein the compound is (S)—N-[8—Methyl-5-(4-methylpiperazin-1-yl)-3,4-dihydro-2H-1-benzopyran-3-yl]-4-(dimethylaminocarbonyl)benzamide or N-(4—Morpholinophenyl)-8-methoxy-5-(4-methylpiperazin-1-yl)-3,4-dihydro-2H-1-benzopyran-3-carboxamide in the form of a free base or pharmaceutical acceptable salt or solvate thereof.

19. A pharmaceutical formulation comprising as active ingredient a therapeutically effective amount of the compound according to claim 1, wherein the compound is an enantiomer or racemate in the form of a free base or a pharmaceutically acceptable salt or solvate thereof optionally in association with diluents, excipients or inert carriers.

20. A method for the treatment of 5-hydroxytryptamine mediated disorders, comprising administering to a patient in need of such treatment a therapeutically effective amount of the pharmaceutical formulation of claim 19.

21. A method for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain, hypertension, urinary incontinence or vasospasm; or for inhibiting tumor growth, comprising administering to a patient in need of such treatment a therapeutically effective amount of the pharmaceutical formulation of claim 19.

22. A method for the treatment of disorders in the central nervous system, comprising administering to a patient in need of such treatment a therapeutically effective amount of the pharmaceutical formulation of claim 19.

23. A method for the treatment of disorders in the central nervous system and/or urinary incontinence or vasospasm, or for inhibiting tumor growth, comprising administering to a mammal in need of such treatment a therapeutically effective amount of a compound defined in claim 1.

24. A method according to claim 22 or 23 wherein the disorders of the central nervous system are mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain or hypertension.

25. A method for the treatment of 5-hydroxytryptamine mediated disorders, compromising administering to a mammal in need of such treatment a therapeutically effective amount of a compound defined in claim 1.

26. A process for the preparation of the compound of formula I according to claim 1, comprising:

A(i) acylation in the case wherein $R_1$ is $C_1$–$C_6$ alkyl or $C_3$–$C_6$ cycloalkyl, Y is $NR_2CO$, $R_2$ is hydrogen and X, $R_3$ and $R_9$ are as defined claim 1, of a compound of formula A

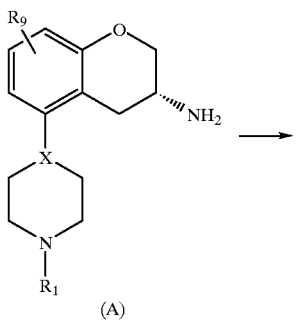

(A)

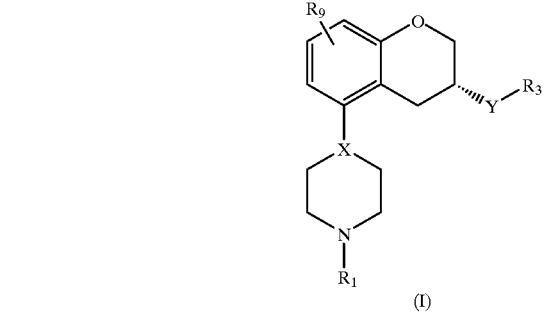

(I)

with an activated carboxylic acid $R_3$—$COLg_1$ wherein $Lg_1$ is a leaving group or with a carboxylic acid $R_3$—COOH and an activating reagent;

A (ii) acylation, in the case wherein $R_1$ is $C_1$–$C_6$ alkyl or $C_3$–$C_6$ cycloalkyl, Y is $NR_2CO$, $R_2$ is $C_1$–$C_6$ alkyl and X, $R_3$ and $R_9$ are as defined in claim 1, of a compound of formula B

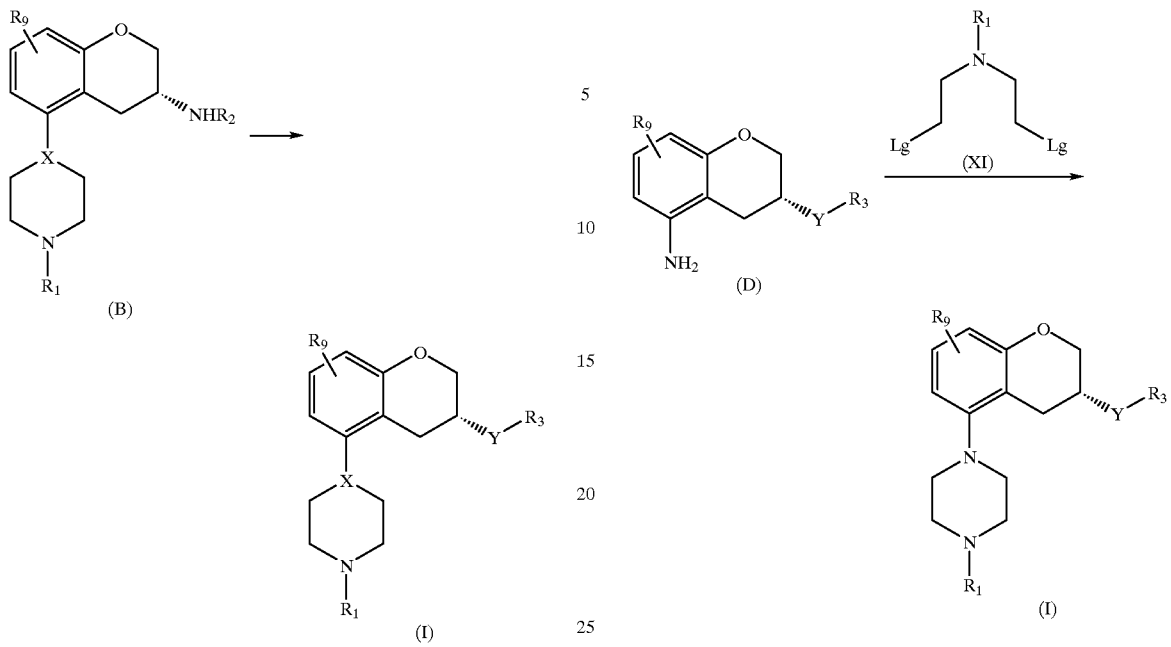

(B)

(I)

with an activated carboxylic acid $R_3$—$COLg_1$ wherein $Lg_1$ is a leaving group or with a carboxylic acid $R_3$—COOH and activating reagent;

A (iii) acylation, in the case wherein $R_1$ and $R_2$ are hydrogen, Y is $NR_2CO$, $R_d$ is a protecting group and X, $R_3$ and $R_9$ are as defined in claim 1, of a compound of formula C (C)

(I)

with an activated carboxylic acid $R_3$—$COLg_1$ wherein $Lg_1$ is a leaving group or with a carboxylic acid $R_3$—COOH and an activating reagent, and removing the protecting group $R_d$;

B (i) reacting, in the case wherein Y is $CONR_2$ and $R_2$, $R_3$ and $R_9$ are as defined in claim 1, a compound of formula D

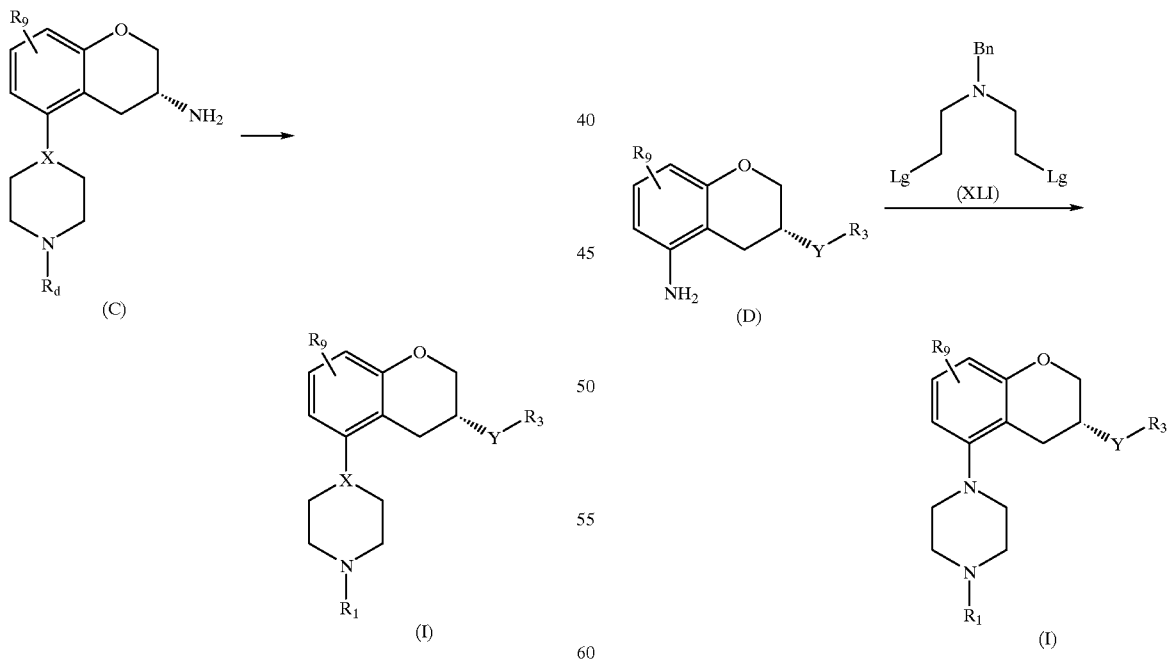

(D)

(I)

with a compound of formula XI wherein Lg is a leaving group;

B (ii) reacting, in the case wherein Y is $CONR_2$, $R_1$ is H and $R_2$, $R_3$ and $R_9$ are as defined in general formula I above with the exception of when $R_4$ and $R_9$ are substituents that are susceptible to catalytic hydrogenation known by a person skilled in the art, a compound of formula D (D)

(I)

with a compound of formula XLI wherein Lg is a leaving group;

C (i) reacting, in the case wherein Y is $NR_2SO_2$, $R_2$ is hydrogen and $R_1$, $R_3$ and $R_9$ are as defined in claim 1, a compound of formula E

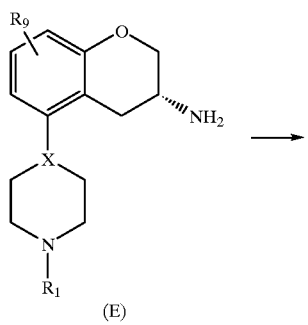

(E)

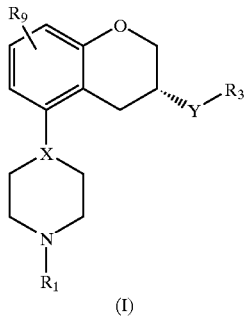

(I)

with an appropriate activated sulfonic acid $R_3SO_2Lg_1$, wherein $Lg_1$ is a leaving group;

C (ii) reacting, in the case wherein Y is $NR_2SO_2$, $R_2$ is $C_1$–$C_6$ alkyl and $R_1$, $R_3$ and $R_9$ are as defined in claim 1, a compound of formula E

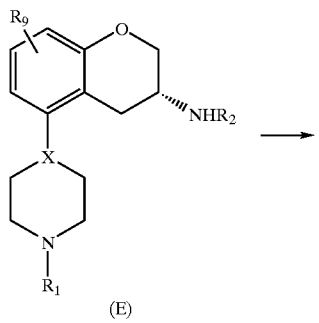

(E)

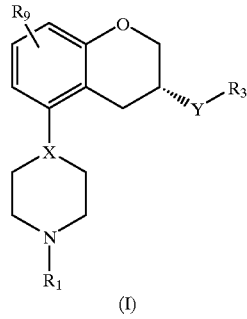

(I)

with an appropriate activated sulfonic acid $R_3SO_2Lg_1$, wherein $Lg_1$ is a leaving group;

D reducing a compound of claim 1, wherein Y is $CONR_2$, and X, $R_1$, $R_2$, $R_3$ and $R_9$ are as defined in claim 1 with the exception of when $R_4$ and $R_9$ are substituents that are susceptible to certain reducing agents known by a person skilled in the art,

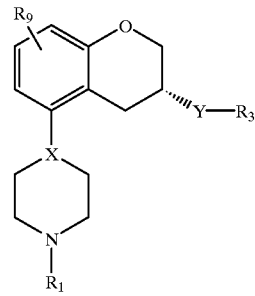

(I)

with an appropriate reducing agent to yield a compound of claim 1 wherein Y is $CH_2NR_2$, and X, $R_1$, $R_2$, $R_3$, and $R_9$ are as defined in claim 1.

27. The method according to claim 23 or 25, wherein the mammal is a human.

* * * * *

UNITED STATES PATENT AND TRADEMARK OFFICE
CERTIFICATE OF CORRECTION

PATENT NO. : 6,387,899 B1  
DATED : May 14, 2002  
INVENTOR(S) : Berg et al.

It is certified that error appears in the above-identified patent and that said Letters Patent is hereby corrected as shown below:

Column 10,  
Lines 50-55, that portion of the formula reading " $NH_2$ " should read -- $NH_2$ --:

Column 11,  
Lines 5-13 and 25-43, (2 instances) that portion of the formula reading " $N—(Bn)_2$ " should read -- $N—(Bn)_2$ --:

Column 12,  
Lines 5-25, (2 instances) and 48-65 (2 instances), that portion of the fomula reading " $N—(Bn)_2$ " should read -- $N—(Bn)_2$ --:

Column 14,  
Lines 1-30 (2 instances), that portion of the formula reading " $N—(Bn)_2$ " should read -- $N—(Bn)_2$ --:

Column 15,  
Lines 13-25 and 33-45, that portion of the formula reading " $N—(Bn)_2$ " should read -- $N—(Bn)_2$ --:

Lines 45-60, that portion of the formula reading " $NH_2$ " should read -- $NH_2$ --:

Column 16,  
Lines 23-35, that portion of the formula reading " $N—(Bn)_2$ " should read -- $N—(Bn)_2$ --:

Column 17,  
Lines 15-30, that portion of the formula reading " $NH_2$ " should read -- $NH_2$ --:  
Lines 30-43, that portion of the formula reading " $NHCOR_2$ " should read -- $NHCOR_2$ --:

Column 18,  
Lines 3-15, that portion of the formula reading " $NHR_2$ " should read -- $NHR_2$ --:

Lines 25-50 (2 instances), that portion of the formula reading " $N—(Bn)_2$ " should read -- $N—(Bn)_2$ --:

UNITED STATES PATENT AND TRADEMARK OFFICE
CERTIFICATE OF CORRECTION

PATENT NO. : 6,387,899 B1  Page 2 of 5
DATED : May 14, 2002
INVENTOR(S) : Berg et al.

It is certified that error appears in the above-identified patent and that said Letters Patent is hereby corrected as shown below:

Column 19,
Lines 5-20, that portion of the formula reading " $\text{N—(Bn)}_2$ " should read -- $\text{N—(Bn)}_2$ --:
Lines 20-33, (2 instances) and 40-60 (2 instances), that portion of the formula reading " $\text{NH}_2$ " should read -- $\text{NH}_2$ --:
Lines 58-65, that portion of the formula reading " $\text{CO}_2\text{C}_2\text{H}_5$ " should read -- $\text{CO}_2\text{C}_2\text{H}_5$ --:

Column 20,
Lines 1-10, that portion of the formula reading " $\text{CO}_2\text{C}_2\text{H}_5$ " should read -- $\text{CO}_2\text{C}_2\text{H}_5$ --:

Lines 35-43, that portion of the formula reading " COOH " should read -- COOH --:

Lines 43-50, that portion of the formula reading " $\text{Y}-\text{R}_3$ " should read -- $\text{Y}-\text{R}_3$ --:

Column 21,
Lines 1-10, that portion of the formula reading " $\text{Y}-\text{R}_3$ " should read -- $\text{Y}-\text{R}_3$ --:

Lines 33-40, that portion of the formula reading " $\text{CO}_2\text{R}_e$ " should read -- $\text{CO}_2\text{R}_e$ --:

Column 22,
Lines 10-15, that portion of the formula reading " $\text{CO}_2\text{H}$ " should read -- $\text{CO}_2\text{H}$ --:

Column 23,
Lines 3-10, that portion of the formula reading " $\text{CO}_2\text{C}_2\text{H}_5$ " should read -- $\text{CO}_2\text{C}_2\text{H}_5$ --:
Lines 13-20, that portion of the formula reading " $\text{NH}_2$ " should read -- $\text{NH}_2$ --:

Lines 40-65 (2 instances), that portion of the formula reading " $\text{N—(Bn)}_2$ " should read -- $\text{N—(Bn)}_2$ --:

Column 24,
Lines 23-35, that portion of the formula reading " $\text{N—(Bn)}_2$ " should read -- $\text{N—(Bn)}_2$ --:
Lines 38-50, that portion of the formula reading " $\text{NH}_2$ " should read -- $\text{NH}_2$ --:

UNITED STATES PATENT AND TRADEMARK OFFICE
CERTIFICATE OF CORRECTION

PATENT NO. : 6,387,899 B1
DATED : May 14, 2002
INVENTOR(S) : Berg et al.

It is certified that error appears in the above-identified patent and that said Letters Patent is hereby corrected as shown below:

Column 25,
Lines 5-18, that portion of the formula reading " $NH_2$ " should read -- $NHR_2$ --:

Lines 30-43, that portion of the formula reading " $N—(Bn)_2$ " should read -- $N—(Bn)_2$ --:

Column 26,
Lines 1-13, that portion of the formula reading " $NH_2$ " should read -- $NH_2$ --:

Lines 15-26, that portion of the formula reading " $Y—R_3$ " should read -- $Y—R_3$ --:
Lines 55-65, that portion of the formula reading " $NH_2$ " should read -- $NH_2$ --:

Column 27,
Lines 1-13 and 50-60, that portion of the formula reading " $Y—R_3$ " should read -- $Y—R_3$ --:

Lines 38-50, that portion of the formula reading " $NH_2$ " should read -- $NH_2$ --:

Column 28,
Lines 25-40 (2 instances), that portion of the formula reading " $Y—R_3$ " should read -- $Y—R_3$ --:

Column 29,
Lines 1-25, (2 instances), that portion of the formula reading " $Y—R_3$ " should read -- $Y—R_3$ --:

Lines 55-65, that portion of the formula reading " $NH_2$ " should read -- $NH_2$ --:

Column 30,
Lines 1-13 and 40-50, that portion of the formula reading " $Y—R_3$ " should read -- $Y—R_3$ --:

Lines 27-38, that portion of the formula reading " $NHR_2$ " should read -- $NHR_2$ --:

UNITED STATES PATENT AND TRADEMARK OFFICE
CERTIFICATE OF CORRECTION

PATENT NO. : 6,387,899 B1
DATED : May 14, 2002
INVENTOR(S) : Berg et al.

It is certified that error appears in the above-identified patent and that said Letters Patent is hereby corrected as shown below:

Column 31,
Lines 1-13 and 40-53, that portion of the formula reading " [formula with Y-R₃] " should read -- [formula with Y-R₃] --:

Lines 30-40, that portion of the formula reading " [NHR₂] " should read -- [NHR₂] --:

Column 32,
Lines 13-25, that portion of the formula reading " [NHR₂] " should read -- [NHR₂] --:
Lines 48-60, (2 instances) and 40-60 (2 instances), that portion of the formula reading " [NH₂] " should read -- [NH₂] --:

Column 33,
Lines 1-10, that portion of the formula reading " [Y-R₃] " should read -- [Y-R₃] --:

Column 40,
Line 40, delete "soup" and substitute therefor -- group --.

Column 42,
Lines 35-45, that portion of the formula reading " [NH₂] " should read -- [NH₂] --:
Lines 45-58, that portion of the formula reading " [Y-R₃] " should read -- [Y-R₃] --:

Column 43,
Lines 1-13, that portion of the formula reading " [NHR₂] " should read -- [NHR₂] --:

Lines 15-25 and 48-60, that portion of the formula reading " [Y-R₃] " should read -- [Y-R₃] --:

Lines 35-45, that portion of the formula reading " [NH₂] " should read -- [NH₂] --:

UNITED STATES PATENT AND TRADEMARK OFFICE
CERTIFICATE OF CORRECTION

PATENT NO.   : 6,387,899 B1
DATED        : May 14, 2002
INVENTOR(S)  : Berg et al.

It is certified that error appears in the above-identified patent and that said Letters Patent is hereby corrected as shown below:

Column 44,
Lines 1-25 (2 instances) and 40-60 (2 instances), that portion of the formula reading " [structure] " should read -- [structure] --;

Line 28, insert -- $R_1$ is as defined in claim 1 -- before the semicolon.
Lines 31-32, delete "general formula I above" and substitute therefor -- claim 1 --.

Column 45,
Lines 1-13, that portion of the formula reading " $NH_2$ " should read -- $NH_2$ --;

Lines 15-25, that portion of the formula reading " [structure with $R_3$] " should read -- [structure with $R_3$] --;

Lines 35-45, that portion of the formula reading " $NHR_2$ " should read -- $NHR_2$ --;

Column 46,
Lines 1-13 and 25-38, that portion of the formula reading " [structure with $R_3$] " should read -- [structure with $R_3$] --;

Signed and Sealed this

Eighth Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,387,899 B1
DATED        : May 14, 2002
INVENTOR(S)  : Berg et al.

It is certified that error appears in the above-identified patent and that said Letters Patent is hereby corrected as shown below:

Column 10,
Lines 50-55, that portion of the formula reading " $\text{NH}_2$ " should read -- $\text{NH}_2$ --:

Column 11,
Lines 5-13 and 25-43, (2 instances) that portion of the formula reading " $N{-}(Bn)_2$ " should read -- $N{-}(Bn)_2$ --:

Column 12,
Lines 5-25, (2 instances) and 48-65 (2 instances), that portion of the fomula reading " $N{-}(Bn)_2$ " should read -- $N{-}(Bn)_2$ --:

Column 14,
Lines 1-30 (2 instances), that portion of the formula reading " $N{-}(Bn)_2$ " should read -- $N{-}(Bn)_2$ --:

Column 15,
Lines 13-25 and 33-45, that portion of the formula reading " $N{-}(Bn)_2$ " should read -- $N{-}(Bn)_2$ --:

Lines 45-60, that portion of the formula reading " $\text{NH}_2$ " should read -- $\text{NH}_2$ --:

Column 16,
Lines 23-35, that portion of the formula reading " $N{-}(Bn)_2$ " should read -- $N{-}(Bn)_2$ --:

Column 17,
Lines 15-30, that portion of the formula reading " $\text{NH}_2$ " should read -- $\text{NH}_2$ --:
Lines 30-43, that portion of the formula reading " $\text{NHCOR}_2$ " should read -- $\text{NHCOR}_2$ --:

Column 18,
Lines 3-15, that portion of the formula reading " $\text{NHR}_2$ " should read -- $\text{NHR}_2$ --:

Lines 25-50 (2 instances), that portion of the formula reading " $N{-}(Bn)_2$ " should read -- $N{-}(Bn)_2$ --:

UNITED STATES PATENT AND TRADEMARK OFFICE
CERTIFICATE OF CORRECTION

PATENT NO. : 6,387,899 B1  
DATED : May 14, 2002  
INVENTOR(S) : Berg et al.

It is certified that error appears in the above-identified patent and that said Letters Patent is hereby corrected as shown below:

Column 19,  
Lines 5-20, that portion of the formula reading " ⁄⁄⁄N—(Bn)$_2$ " should read -- ⁄⁄⁄N—(Bn)$_2$ --:  
Lines 20-33, that portion of the formula reading " ⁄⁄⁄NH$_2$ " should read -- ⁄⁄⁄NH$_2$ --:

Lines 58-65, that portion of the formula reading " ⁄⁄⁄CO$_2$C$_2$H$_5$ " should read -- ⁄⁄⁄CO$_2$C$_2$H$_5$ --:

Column 20,  
Lines 1-10, that portion of the formula reading " ⁄⁄⁄CO$_2$C$_2$H$_5$ " should read -- ⁄⁄⁄CO$_2$C$_2$H$_5$ --:

Lines 35-43, that portion of the formula reading " ⁄⁄⁄COOH " should read -- ⁄⁄⁄COOH --:

Lines 43-50, that portion of the formula reading " ⁄⁄⁄Y—R$_3$ " should read -- ⁄⁄⁄Y—R$_3$ --:

Column 21,  
Lines 1-10, that portion of the formula reading " ⁄⁄⁄Y—R$_3$ " should read -- ⁄⁄⁄Y—R$_3$ --:

Lines 33-40, that portion of the formula reading " ⁄⁄⁄CO$_2$R$_e$ " should read -- ⁄⁄⁄CO$_2$R$_e$ --:

Column 22,  
Lines 10-15, that portion of the formula reading " ⁄⁄⁄CO$_2$H " should read -- ⁄⁄⁄CO$_2$H --:

Column 23,  
Lines 3-10, that portion of the formula reading " ⁄⁄⁄CO$_2$C$_2$H$_5$ " should read -- ⁄⁄⁄CO$_2$C$_2$H$_5$ --:  
Lines 13-20, that portion of the formula reading " ⁄⁄⁄NH$_2$ " should read -- ⁄⁄⁄NH$_2$ --:

Lines 40-65 (2 instances), that portion of the formula reading " ⁄⁄⁄N—(Bn)$_2$ " should read -- ⁄⁄⁄N—(Bn)$_2$ --:

Column 24,  
Lines 23-35, that portion of the formula reading " ⁄⁄⁄N—(Bn)$_2$ " should read -- ⁄⁄⁄N—(Bn)$_2$ --:  
Lines 38-50, that portion of the formula reading " ⁄⁄⁄NH$_2$ " should read -- ⁄⁄⁄NH$_2$ --:

UNITED STATES PATENT AND TRADEMARK OFFICE
CERTIFICATE OF CORRECTION

PATENT NO. : 6,387,899 B1
DATED : May 14, 2002
INVENTOR(S) : Berg et al.

It is certified that error appears in the above-identified patent and that said Letters Patent is hereby corrected as shown below:

Column 25,
Lines 5-18, that portion of the formula reading " $\overset{\prime\prime\prime\prime}{N}HR_2$ " should read -- $\overset{w}{N}HR_2$ --;

Lines 30-43, that portion of the formula reading " $\overset{\prime\prime\prime\prime}{N}-(Bn)_2$ " should read -- $\overset{w}{N}-(Bn)_2$ --;

Column 26,
Lines 1-13, that portion of the formula reading " $\overset{\prime\prime\prime\prime}{N}H_2$ " should read -- $\overset{w}{N}H_2$ --;

Lines 15-26, that portion of the formula reading "  " should read -- $\overset{w}{Y}-R_3$ --;
Lines 55-65, that portion of the formula reading " $\overset{\prime\prime\prime\prime}{N}H_2$ " should read -- $\overset{w}{N}H_2$ --;

Column 27,
Lines 1-13 and 50-60, that portion of the formula reading "  " should read -- $\overset{w}{Y}-R_3$ --;

Lines 38-50, that portion of the formula reading " $\overset{\prime\prime\prime\prime}{N}H_2$ " should read -- $\overset{w}{N}H_2$ --;

Column 28,
Lines 25-40 (2 instances), that portion of the formula reading "  "
should read  -- $\overset{w}{Y}-R_3$ --;

Column 29,
Lines 1-25, (2 instances), that portion of the formula reading "  " should
read  -- $\overset{w}{Y}-R_3$ --;

Lines 55-65, that portion of the formula reading " $\overset{\prime\prime\prime\prime}{N}H_2$ " should read -- $\overset{w}{N}H_2$ --;

Column 30,
Lines 1-13 and 40-50, that portion of the formula reading "  " should read -- $\overset{w}{Y}-R_3$ --;

Lines 27-38, that portion of the formula reading " $\overset{\prime\prime\prime\prime}{N}HR_2$ " should read -- $\overset{w}{N}HR_2$ --;

UNITED STATES PATENT AND TRADEMARK OFFICE
CERTIFICATE OF CORRECTION

PATENT NO. : 6,387,899 B1
DATED : May 14, 2002
INVENTOR(S) : Berg et al.

It is certified that error appears in the above-identified patent and that said Letters Patent is hereby corrected as shown below:

Column 31,
Lines 1-13 and 40-53, that portion of the formula reading " [structure: ⋯Y–R₃] " should read -- [structure: ⋯Y–R₃] --:

Lines 30-40, that portion of the formula reading " [structure: ⋯NHR₂] " should read -- [structure: ⋯NHR₂] --:

Column 32,
Lines 13-25, that portion of the formula reading " [structure: ⋯NHR₂] " should read -- [structure: ⋯NHR₂] --:
Lines 48-60, that portion of the formula reading " [structure: ⋯NH₂] " should read -- [structure: ⋯NH₂] --:

Column 33,
Lines 1-10, that portion of the formula reading " [structure: ⋯Y–R₃] " should read -- [structure: ⋯Y–R₃] --:

Column 40,
Line 40, delete "soup" and substitute therefor -- group --.

Column 42,
Lines 35-45, that portion of the formula reading " [structure: ⋯NH₂] " should read -- [structure: ⋯NH₂] --:
Lines 45-58, that portion of the formula reading " [structure: ⋯Y–R₃] " should read -- [structure: ⋯Y–R₃] --:

Column 43,
Lines 1-13, that portion of the formula reading " [structure: ⋯NHR₂] " should read -- [structure: ⋯NHR₂] --:

Lines 15-25 and 48-60, that portion of the formula reading " [structure: ⋯Y–R₃] " should read -- [structure: ⋯Y–R₃] --:

Lines 35-45, that portion of the formula reading " [structure: ⋯NH₂] " should read -- [structure: ⋯NH₂] --:

UNITED STATES PATENT AND TRADEMARK OFFICE
CERTIFICATE OF CORRECTION

PATENT NO. : 6,387,899 B1
DATED : May 14, 2002
INVENTOR(S) : Berg et al.

It is certified that error appears in the above-identified patent and that said Letters Patent is hereby corrected as shown below:

Column 44,
Lines 1-25 (2 instances) and 40-60 (2 instances), that portion of the formula reading " 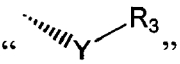 " should read --  --:

Line 28, insert -- and $R_1$ is as defined in claim 1 -- before the semicolon.
Lines 31-32, delete "general formula I above" and substitute therefor -- claim 1 --.

Column 45,
Lines 1-13, that portion of the formula reading " 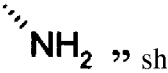 " should read -- 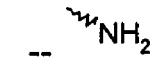 --:

Lines 15-25, that portion of the formula reading "  " should read -- 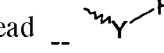 --:

Lines 35-45, that portion of the formula reading "  " should read -- 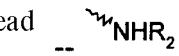 --:

Column 46,
Lines 1-13 and 25-38, that portion of the formula reading " 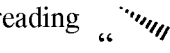 " should read -- 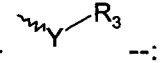 --:

This certificate supersedes Certificate of Correction issued October 8, 2002.

Signed and Sealed this

Twelfth Day of August, 2003

JAMES E. ROGAN
*Director of the United States Patent and Trademark Office*